(12) United States Patent
Kim et al.

(10) Patent No.: US 9,012,230 B2
(45) Date of Patent: Apr. 21, 2015

(54) FLUORESCENT NANOPROBE FOR DETECTING HYDROGEN PEROXIDE AND FABRICATION METHOD THEREOF

(75) Inventors: Sehoon Kim, Seoul (KR); Ick Chan Kwon, Seoul (KR); Jai Kyeong Kim, Seoul (KR); Chang-Keun Lim, Seoul (KR); Jeongyun Heo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 369 days.

(21) Appl. No.: 13/362,183

(22) Filed: Jan. 31, 2012

(65) Prior Publication Data

US 2012/0276651 A1      Nov. 1, 2012

(30) Foreign Application Priority Data

Apr. 26, 2011   (KR) .................. 10-2011-0039143

(51) Int. Cl.

| | | |
|---|---|---|
| *G01N 21/64* | (2006.01) | |
| *C07D 239/60* | (2006.01) | |
| *C07C 255/36* | (2006.01) | |
| *C07C 255/40* | (2006.01) | |
| *C07C 255/41* | (2006.01) | |
| *C07C 309/73* | (2006.01) | |
| *C07C 317/46* | (2006.01) | |
| *C07D 403/10* | (2006.01) | |
| *C07C 69/732* | (2006.01) | |
| *C07C 39/373* | (2006.01) | |
| *C07C 69/94* | (2006.01) | |
| *C07C 47/565* | (2006.01) | |
| *C07C 49/248* | (2006.01) | |
| *C07C 49/747* | (2006.01) | |

(52) U.S. Cl.
CPC ............ *C07D 239/60* (2013.01); *C07C 255/36* (2013.01); *C07C 255/40* (2013.01); *C07C255/41* (2013.01); *C07C 309/73* (2013.01); *C07C 317/46* (2013.01); *C07C 2102/08* (2013.01); *C07D 403/10* (2013.01); *C07C 69/732* (2013.01); *C07C 39/373* (2013.01); *C07C 69/94* (2013.01); *C07C 47/565* (2013.01); *C07C 49/248* (2013.01); *C07C 49/747* (2013.01)

(58) Field of Classification Search
CPC .. C12Q 1/28; C12Q 2326/00; G01N 33/0039; G01N 21/766; G01N 21/783; C08K 5/1345; C08K 5/375; C08K 5/315; C09K 15/08; A61Q 17/04; B41M 5/3335; A61K 8/40; C09B 57/04; C09B 23/10; C09B 23/107; C09B 23/105; C09B 23/04; C07C 69/88; C07C 67/317; C07C 67/333; C07C 323/00; C07C 69/732; C07C 65/05; C07C 51/48; C07C 51/00; C07C 51/367; C07C 255/00; C07C 255/41; C07C 309/66; C07C 309/73
USPC ....... 436/135; 560/70, 75; 562/476; 558/401, 558/46; 568/308, 327; 544/300
See application file for complete search history.

(56) References Cited

U.S. PATENT DOCUMENTS

2004/0162397 A1\* 8/2004 Lee et al. .................. 525/420

OTHER PUBLICATIONS

Selective Fluorescence Quenching by Group 8 Metal Ions of a Water-Soluble Poly(p-phenylene vinylene) Derivative Bearing Oligo(oxyethylene) Pendants Kyu-Nam Kim, Young-Wan Kwon, Dong Hoon Choi, Jung-Il Jin Macromol. Chem. Phys. 2009, 210, 1372-1378.\*
Korean Office Action dated Feb. 21, 2013, issued in corresponding Korean Patent Application No. 10-2011-0039143.
Chemical Abstract Accession No. 91:6410, May 12, 1984.
Chemical Abstract Accession No. 143:429750, Nov. 24, 2005.

\* cited by examiner

*Primary Examiner* — Krishnan S Menon
*Assistant Examiner* — Dwan A Gerido
(74) *Attorney, Agent, or Firm* — Goldilocks Zone IP Law

DT

AD

DM

NN

SN

TM

(57) ABSTRACT

The present disclosure relates to a sulfonated benzene compound emitting fluorescence by reaction with hydrogen peroxide, aqueous-dispersed fluorescent nanoprobes applicable for real-time detection of hydrogen peroxide, and a fluorescent nanoprobe fabrication method. The fluorescent nanoprobe contains the following sulfonated benzene compound and water.

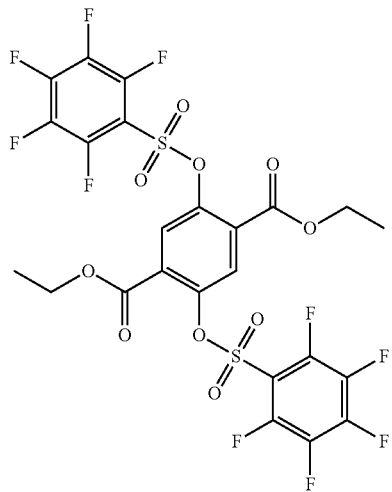

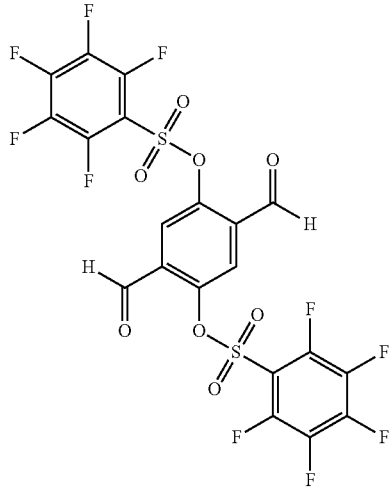

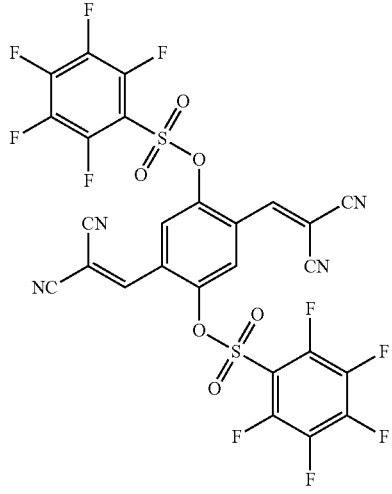

-continued

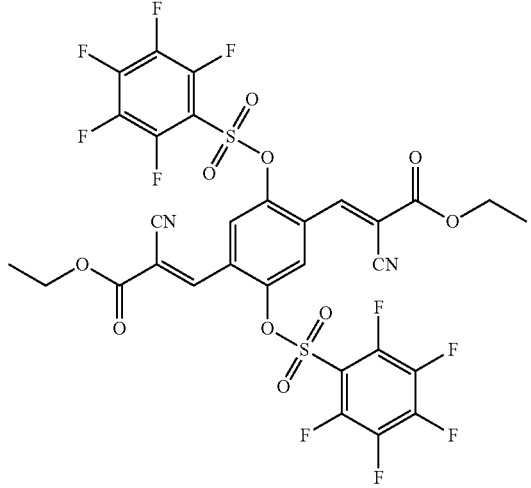

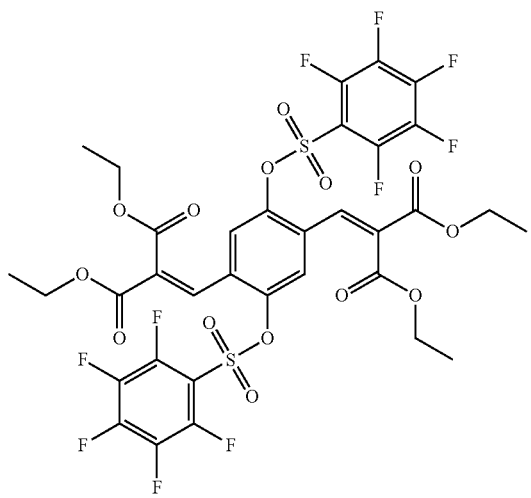

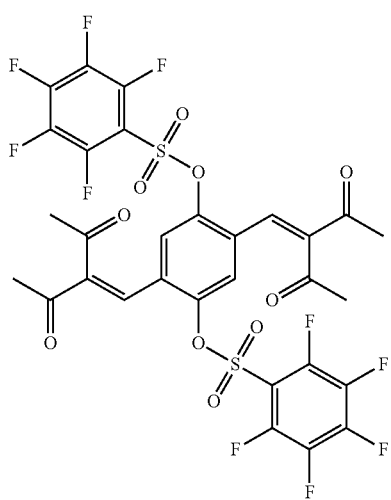

-continued
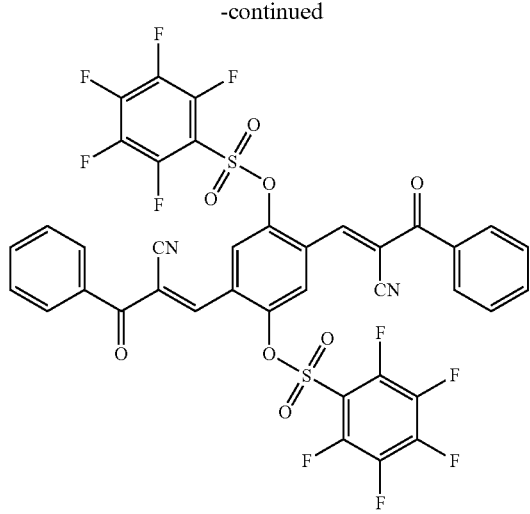
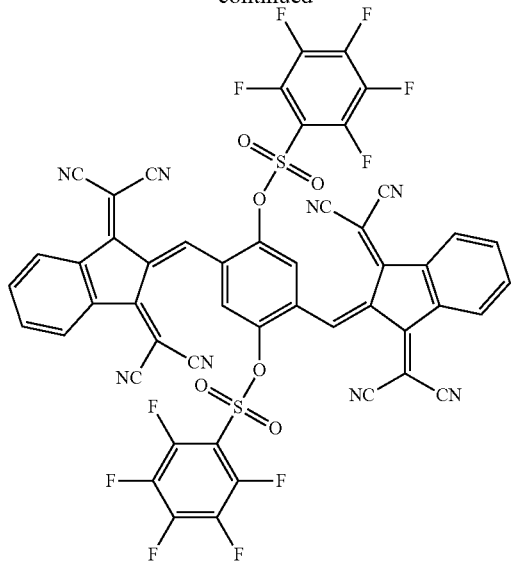
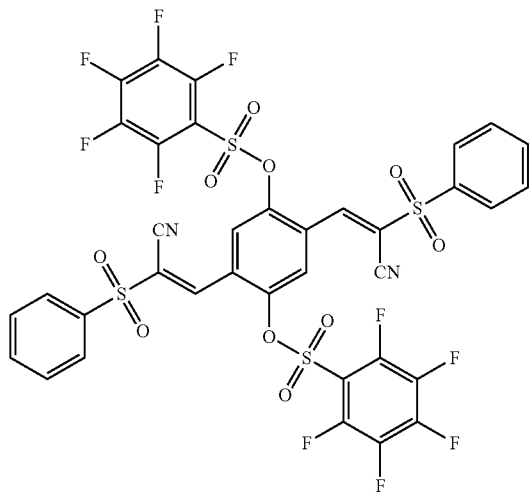
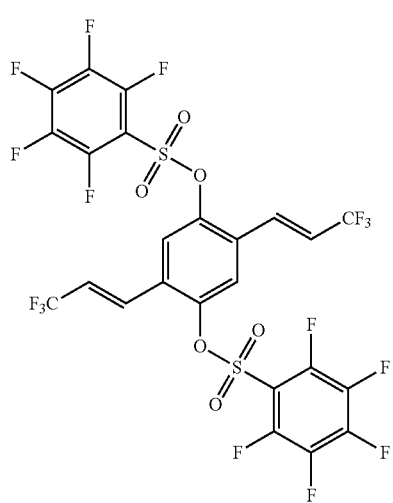
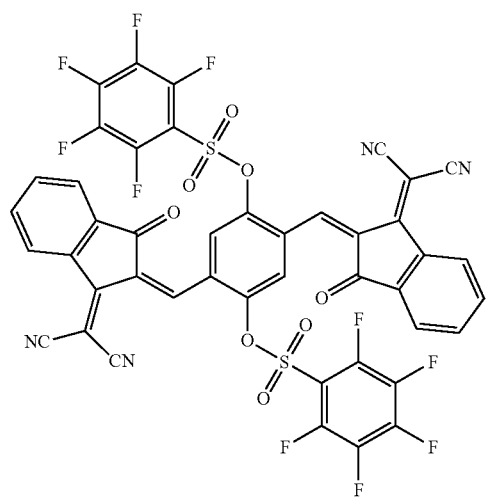

-continued
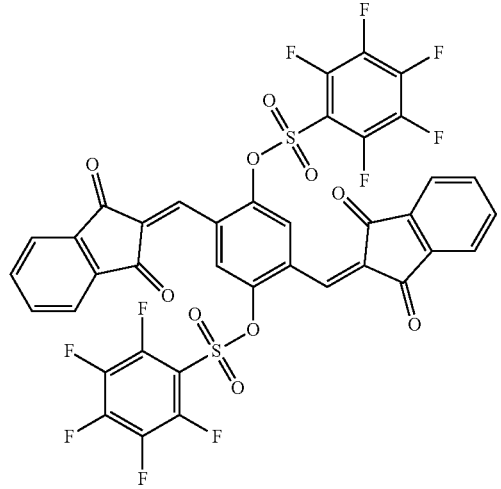
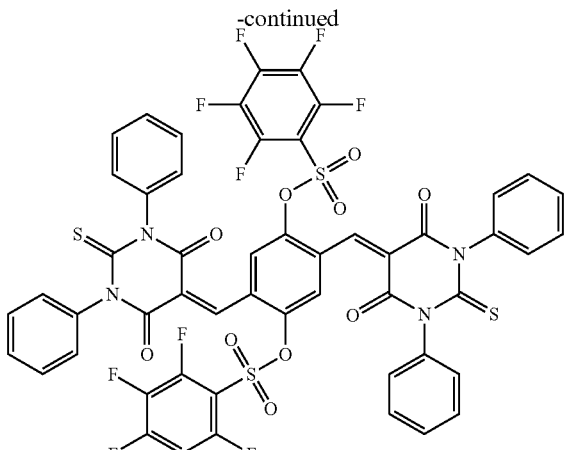
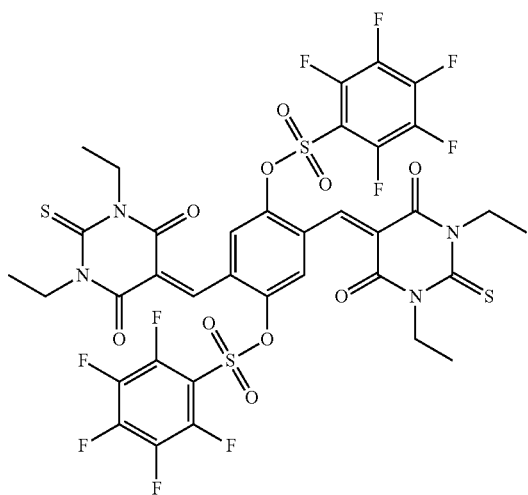
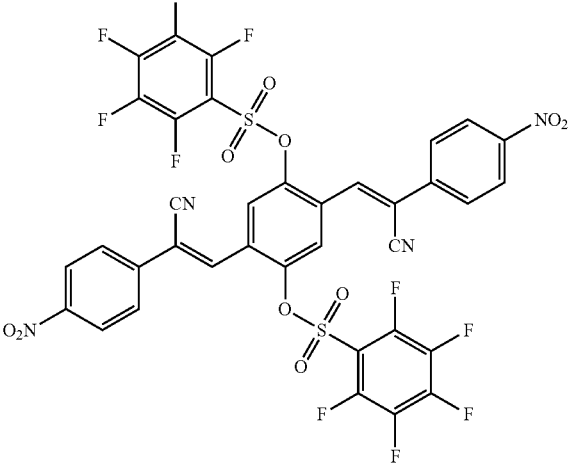
10 Claims, 6 Drawing Sheets

FLUORESCENT NANOPROBE FOR DETECTING HYDROGEN PEROXIDE AND FABRICATION METHOD THEREOF

CROSS-REFERENCE TO RELATED APPLICATION

This application claims the benefit of Korean Patent Application No. 10-2011-0039143, filed on Apr. 26, 2011, which is hereby incorporated by reference for all purposes as if fully set forth herein.

BACKGROUND OF THE INVENTION

1. Field of the Invention

This specification relates to an apparatus for forming an alignment layer, and particularly, to an aqueous-dispersed fluorescent nanoprobe, which contains benzene compound exhibiting fluorescence, sulfonated benzene compound exhibiting fluorescence by reaction with hydrogen peroxide and hydrophobic organic base deriving the fluorescence reaction so as to be applicable for real-time detection of hydrogen peroxide, and a fabrication method thereof.

2. Background of the Invention

Reactive oxygen species (ROS) are essentially generated within a body of aerobe. However, if it is excessively generated or accumulated within the body, it is closely connected with a mechanism, which causes extensive inflammatory diseases, such as cancers, diabetes, Alzheimer's disease, arteriosclerosis, arthritis and the like. Hence, in vivo and in vitro detections of the ROS are very important.

Examples of the ROS include singlet oxygen ($^1O_2$), hydroxyl radical ($OH^-$), superoxide anion ($O_2^-$) and hydrogen peroxide ($H_2O_2$). The others except for the hydrogen peroxide is extremely unstable in a physiological environment, thus to be easily reduced into hydrogen peroxide or water. Hence, in diagnosis of diseases involved in overexpression of ROS, the most advantageous method is to detect hydrogen peroxide, which exhibits the highest stability among ROS and exists in a body in the highest concentration ($1 \times 10^{-7}$ M), in vivo and in vitro.

As representative methods for detecting hydrogen peroxide, a method using fluorescence [Document 1: Novuaki Soh, Anal. Bioanal. Chem. 386: 532-543 (2006)] and a method using chemiluminescence [Document 2: Ahao Lu et al., Trends Anal. Chem. 25: 985-995 (2006), Document 3: Zhenyu Zhang et al. Anal. Chim. Acta 541: 37-47 (2005)] are broadly used.

The detection of the hydrogen peroxide using the chemiluminescence does not require for an irradiation of excitation light, so any background is fluorescence or interference due to the excitation light is not caused. Accordingly, such method has advantage of acquiring high signal-to-noise ratio in spite of its low luminescence efficiency as compared to the fluorescence detection method. Hence, it is very favorable for the in vivo detection. However, such method needs a high-sensitivity detector due to a low absolute signal intensity and is hard to select (determine) a detection time due to disappearance of the luminescence within a short time. Consequently, the detection method using the chemiluminescence has limitation in fabrication of a low-cost sensor for in vivo and in vitro detections.

The fluorescence detection needs excitation light. As compared with the chemiluminescence detection, the fluorescence detection is disadvantageous in that the background fluorescence interferes with detection of a signal. However, the high-sensitivity detector is not needed by virtue of a strong signal and an accumulated signal unlike the chemiluminescence, so the fluorescence detection has no difficulty in determining detection conditions, thereby being effective to fabricate various sensors. The fluorescence detection for hydrogen peroxide is executed by employing a method for measuring fluorescence changes in response to oxidation of fluorescent molecules, which are easily oxidized by the hydrogen peroxide [Document 4: Naoki Umezawa et al. Angew. Chem. Int. Ed. 38: 2899-2901 (1999)], or a method for coupling substituent, which is easily separated by hydrogen peroxide, to fluorescent molecules and measuring changes in fluorescence properties caused by the separation of the substituent [Document 5: Evan W Miller et al., Nat. Chem. Biol. 3: 263-267 (2007), Document 6: Hatsuo Maeda et al., Angew. Chem. 116: 2443-2445 (2004)]. The fluorescence detection method has many advantages, but is not suitable for real-time detection due to taking a long reaction time over 1 hour. Hence, it is the urgent problem to reduce the reaction time for real-time detection.

SUMMARY OF THE INVENTION

Therefore, in order to solve the related art problems, an aspect of the detailed description is to provide a fluorescent probe for detecting hydrogen peroxide, capable of ensuring fast reaction time and high efficiency. More particularly, an aspect of the detailed description is to provide a fluorescent nanoprobe with an enhanced detection reaction rate of hydrogen peroxide by integrating hydrophobic sulfonated benzene compounds generating fluorescence by reaction with hydrogen peroxide and organic bases as a catalyst for accelerating the reaction into a reaction space consisting of nanoparticles, a fabrication method for the nanoprobe, and a detection method for hydrophobic peroxide using the nanoprobe.

A fluorescent benzene compound proposed in this specification may be represented by the following Chemical Formula 1

[Chemical Formula 1]

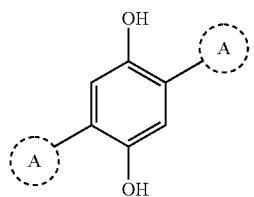

where A denotes at least one electron-accepting substituent selected from a group consisting of ester, aldehyde, nitrile, nitrobenzene, sulfonated benzene, indan, barbituric acid and their derivatives, and the benzene compound may be represented by the following Chemical Formula 2.

[Chemical Formula 2]

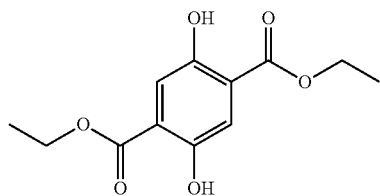

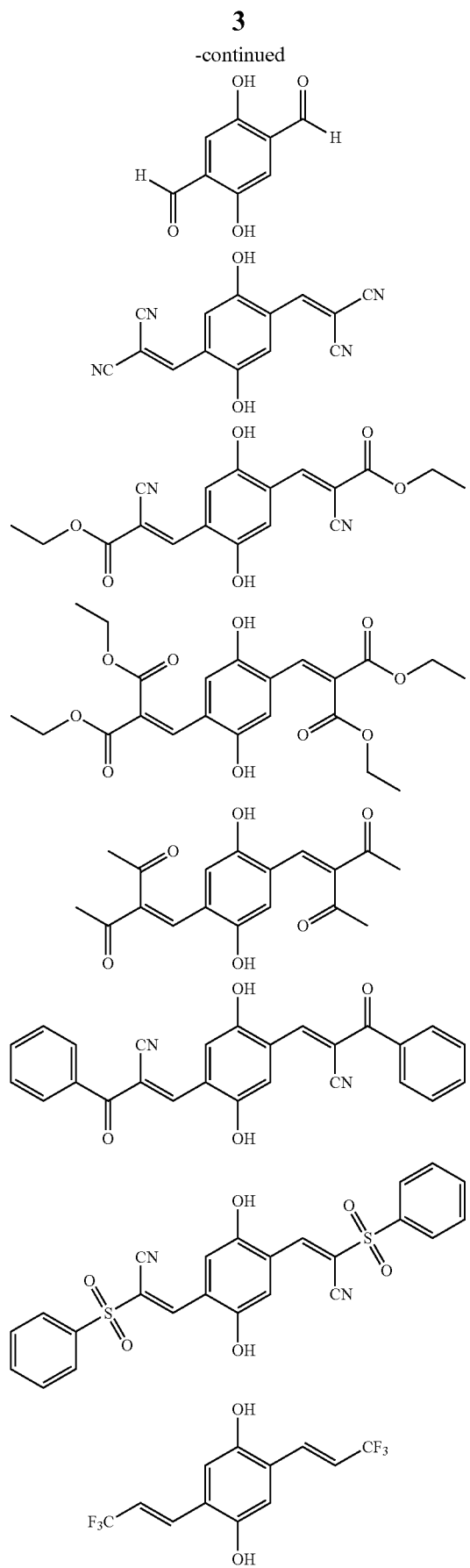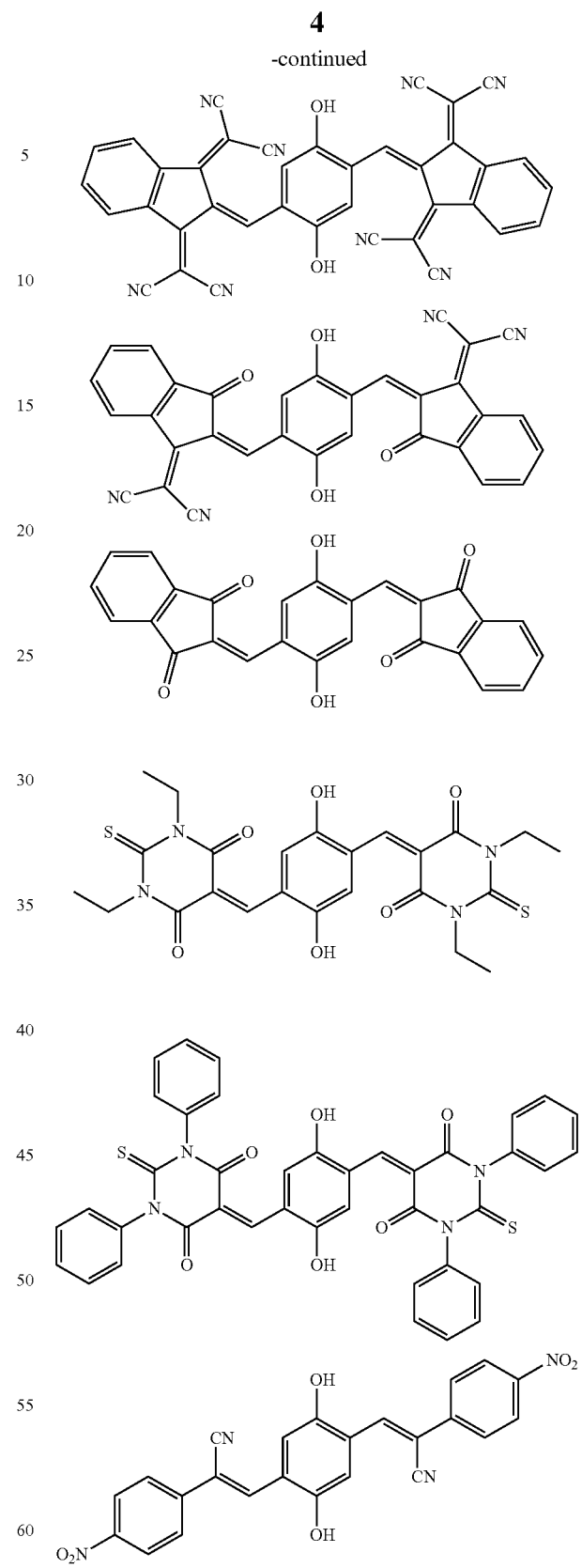
The sulfonated benzene compound proposed in this specification may be a compound from which fluorescence is quenched due to sulfonation, which will be represented by the following Chemical Formula 3.

[Chemical Formula 3]
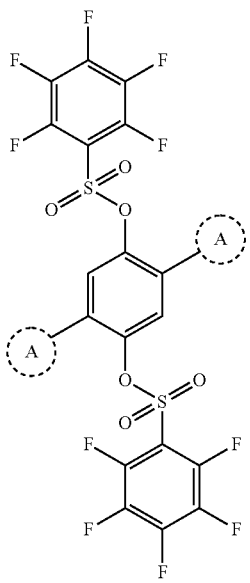
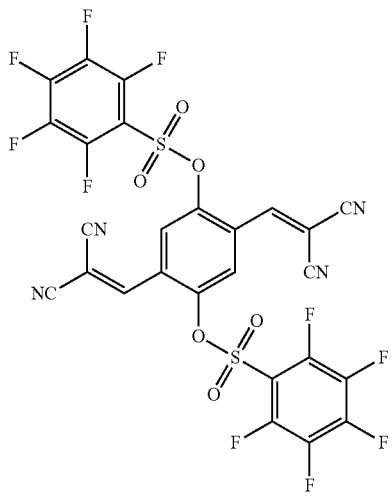
where A denotes at least one electron-accepting substituent selected from a group consisting of ester, aldehyde, nitrile, nitrobenzene, sulfonated benzene, indan, barbituric acid and their derivatives, and the sulfonated benzene compound may be represented by the following Chemical Formula 4.
[Chemical Formula 4]
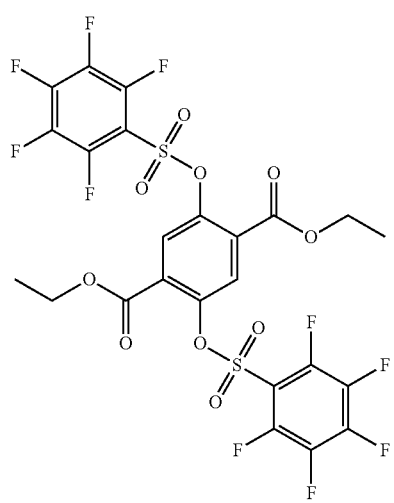
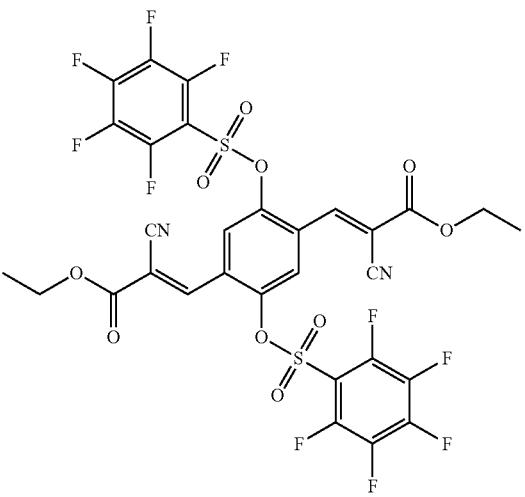
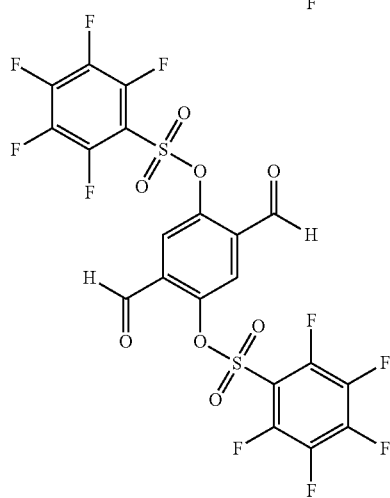
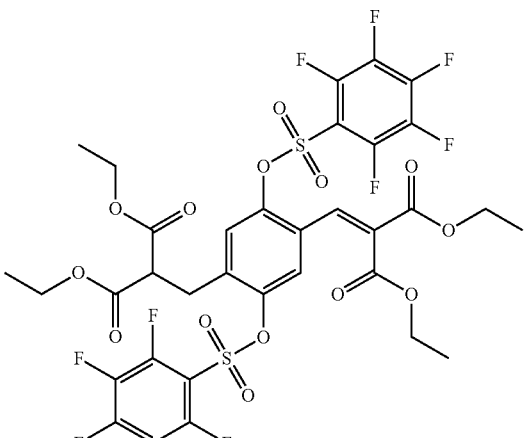

7
-continued
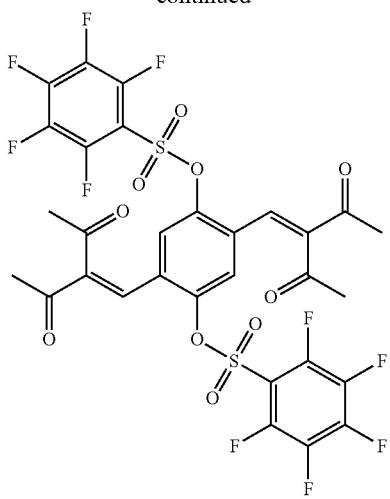
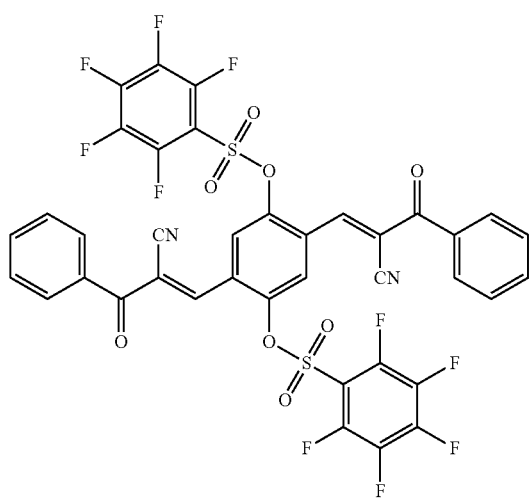
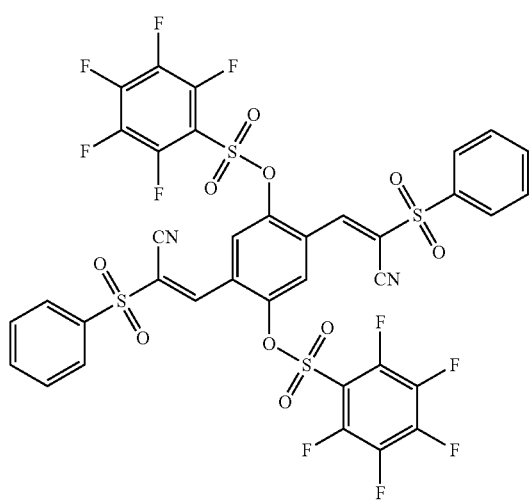
8
-continued
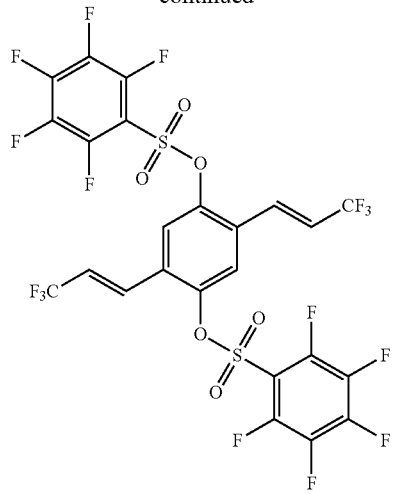
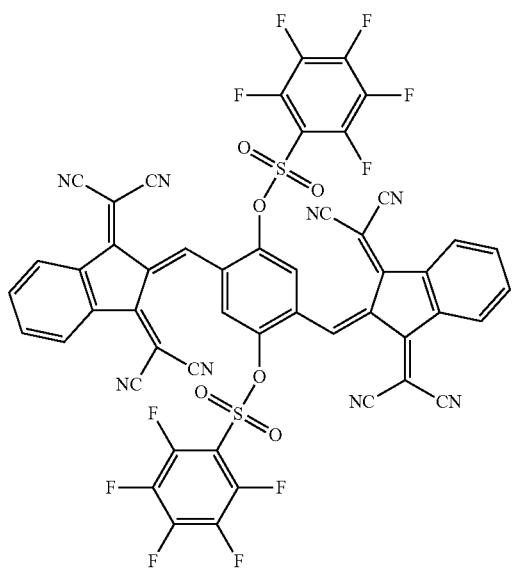
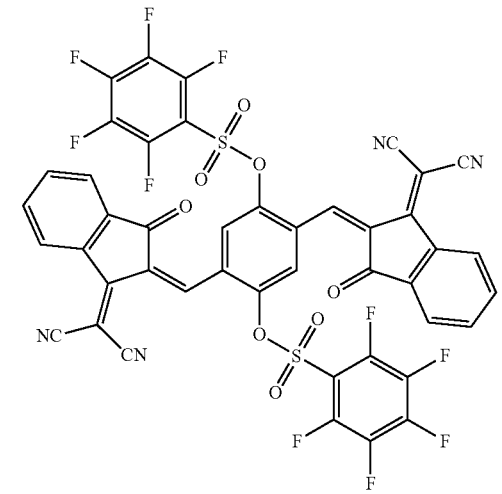

-continued

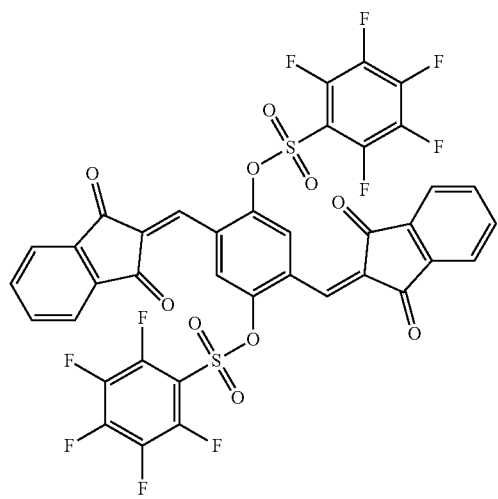

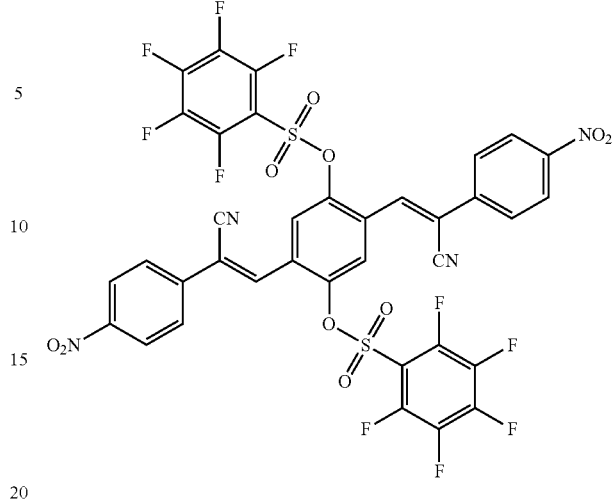

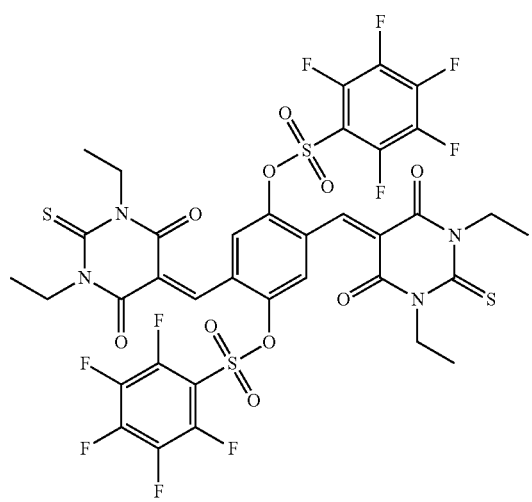

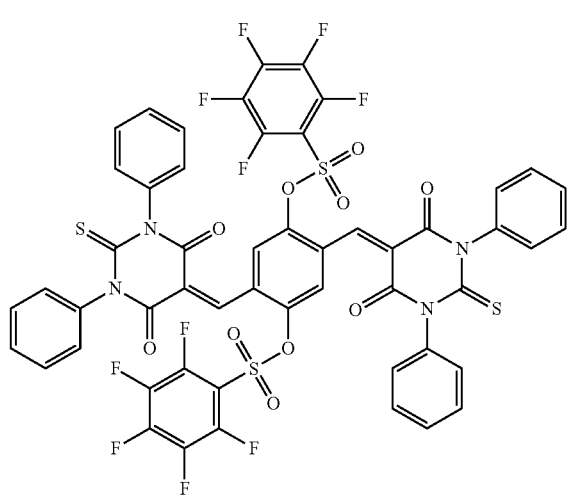

Meanwhile, the fluorescent nanoprobe proposed in this specification may include the sulfonated benzene compound and water.

According to this specification, hydrophobic sulfonated benzene compound contained within aqueous-dispersed fluorescent nanoprobe can emit fluorescence very quickly by virtue of an organic base co-existing within the nanoparticle upon presence of hydrogen peroxide, so as to be used for real-time detection of hydrogen peroxide. Therefore, it can also be used in wide ranges or fields such as cell imaging, in vivo imaging, chemical analysis and the like.

In a state that hydrophobic sulfonated benzene compound sensitive to hydrogen peroxide and hydrophobic organic base are contained within a central portion of the nanoparticle, excellent suspension stability can be exhibited. Also, it may be possible to fabricate effective nanoparticles capable of being extensively applied for detection of hydrogen peroxide in medical and biological fields when using biocompatible polymer surfactant.

The aqueous dispersion of the fluorescent nanoprobes has exhibited a fluorescence increase more than 5 times within several seconds upon reaction with hydrogen peroxide, which allows the fluorescent nanoprobes to be used for real-time detection of the hydrogen peroxide.

The fluorescent molecules can adjust the fluorescence wavelengths according to the electron accepters A shown in FIG. 1, thereby being utilized in wide fields by selecting a suitable fluorescence wavelength according to the use, such as cell imaging, in vivo imaging, chemical analysis and the like.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Figure 1:
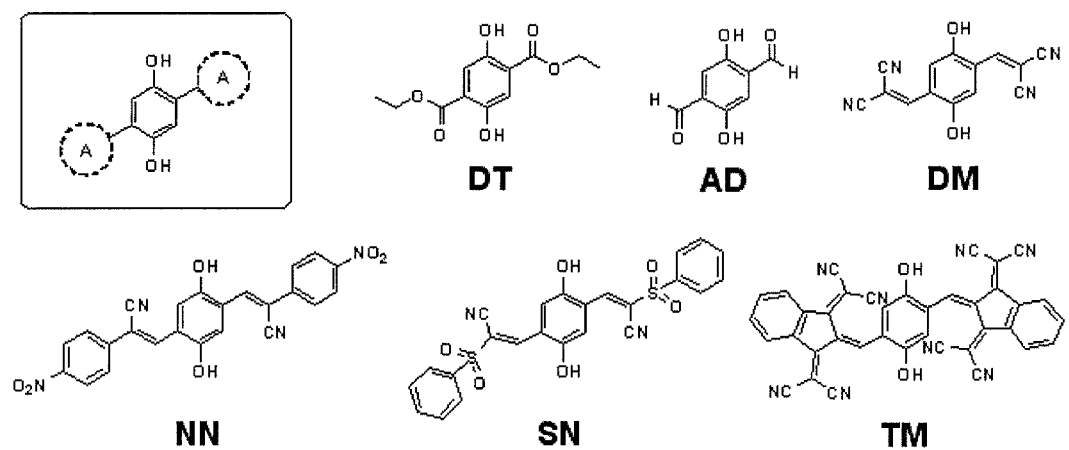
FIG. 1 shows a representative structure of fluorescent molecules fabricated by a method of Examples 1-(1) and 1-(2) and chemical structures of DT, AD, DM, MN, SN and TM, to which electron-accepters A are coupled.

Description will now be given in detail of the exemplary embodiments, with reference to the accompanying drawings.

A benzene compound having fluorescence characteristics proposed in this specification may be represented by Chemical Formula 1 as follows.

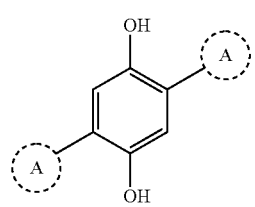

[Chemical Formula 1]

where A denotes at least one electron-accepting substituent selected from a group consisting of ester, aldehyde, nitrile, nitrobenzene, sulfonated benzene, indan, barbituric acid and their derivatives.

According to the electron-accepting substituent A of Chemical Formula 1, the benzene compound may be represented by the following Chemical Formula 2.

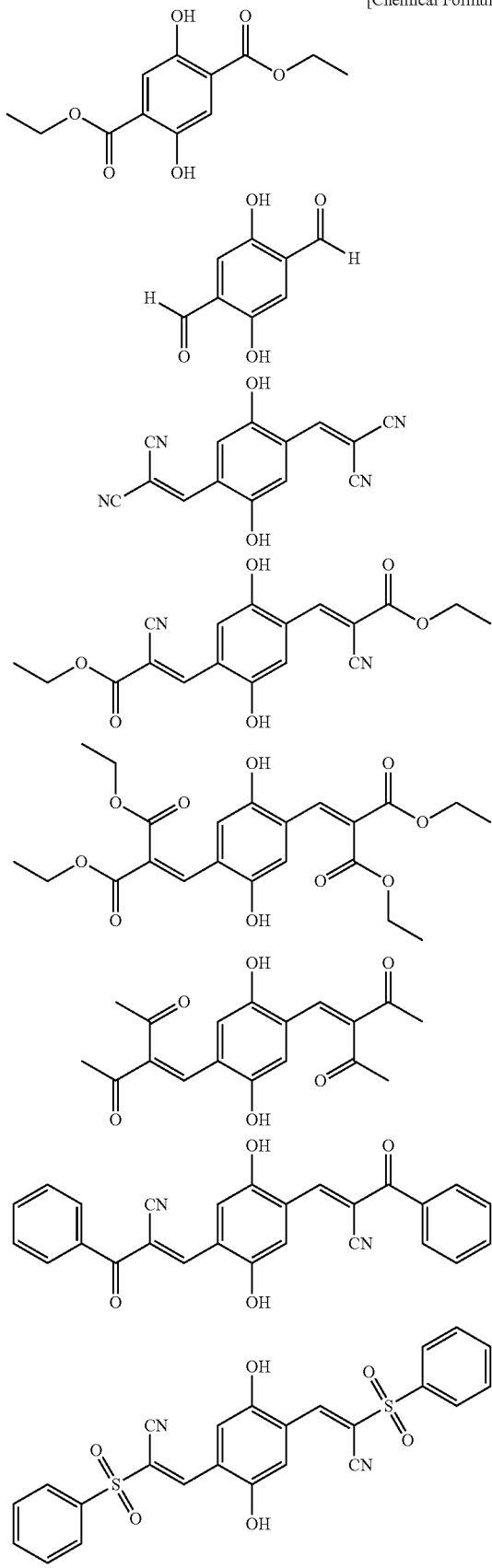

[Chemical Formula 2]

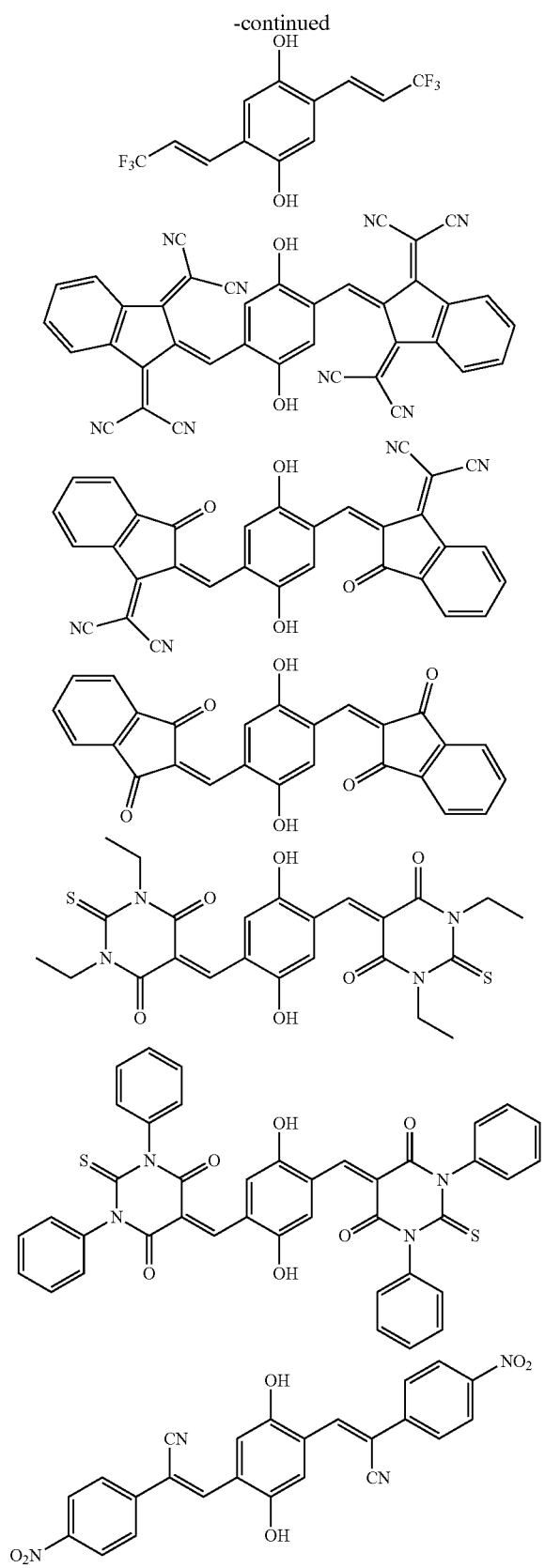

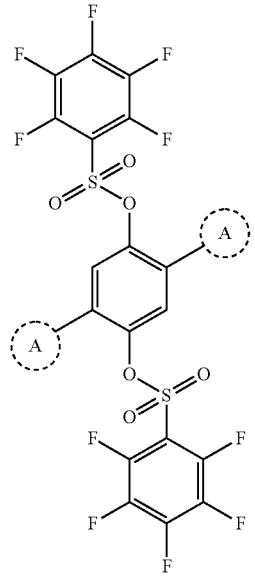

exhibition of fluorescence characteristic to be used for detection and the like. The sulfonated benzene compound may be represented by the following Chemical Formula 3.

[Chemical Formula 3]

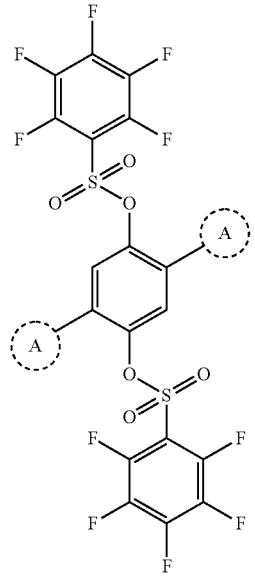

where A denotes at least one electron-accepting substituent selected from a group consisting of ester, aldehyde, nitrile, nitrobenzene, sulfonated benzene, indan, barbituric acid and their derivatives.

According to the substituent A of Chemical Formula 3, the sulfonated benzene compound may be represented by the following Chemical Formula 4.

[Chemical Formula 4]

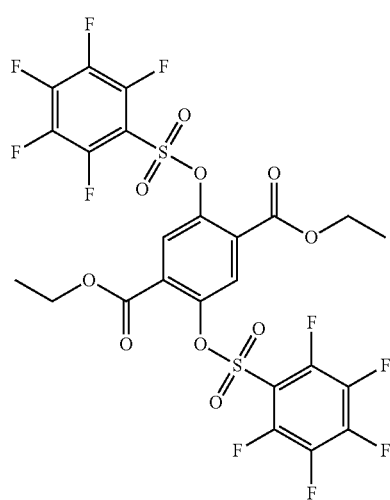

The sulfonated benzene compound proposed in this specification may be a compound, from which fluorescence is quenched due to sulfonation, which is executed to prevent -continued
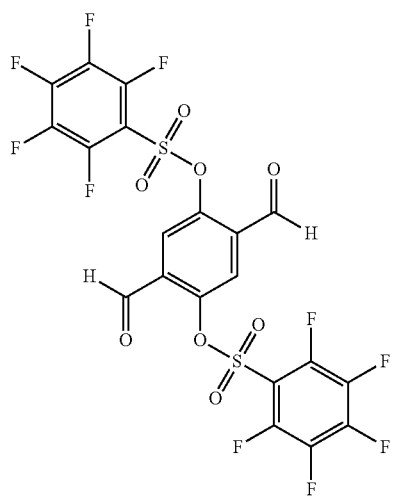
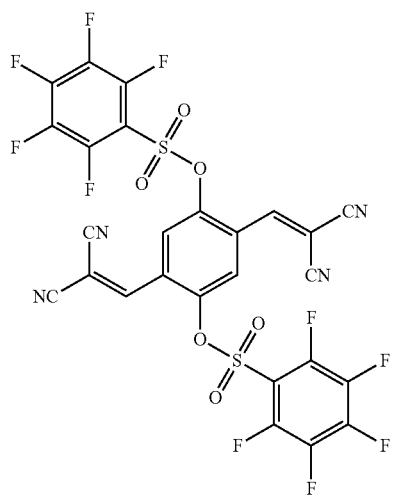
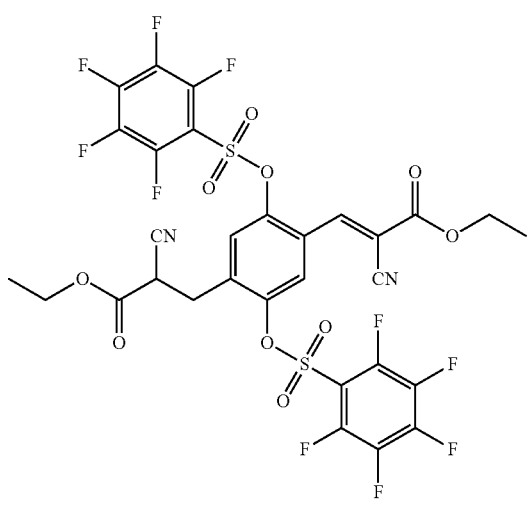
-continued
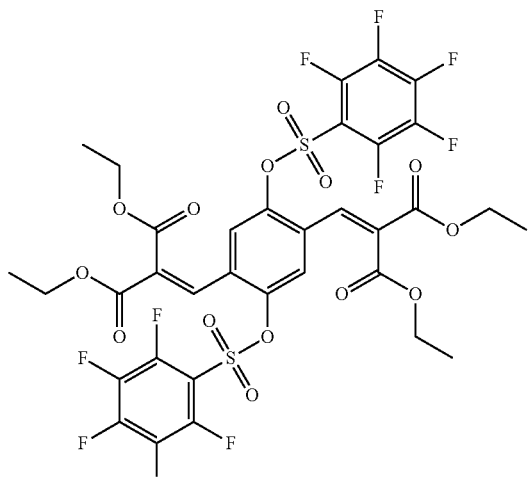
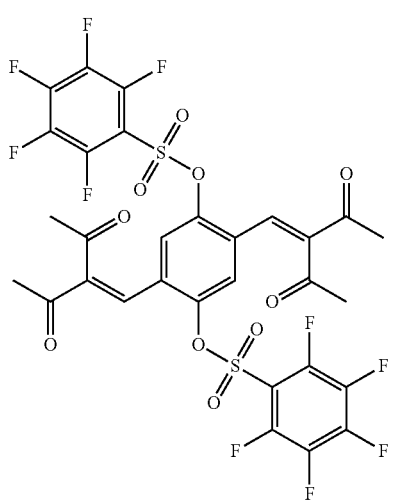
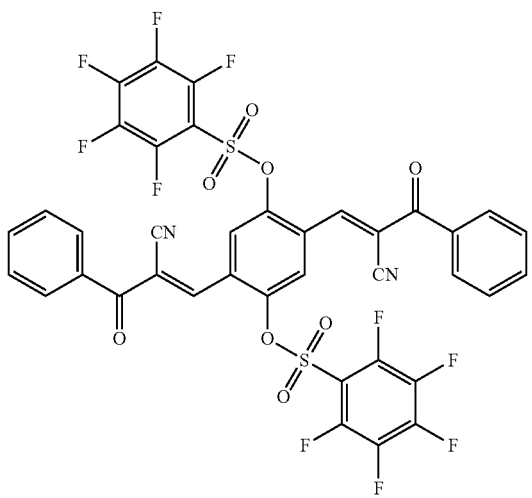

17
-continued
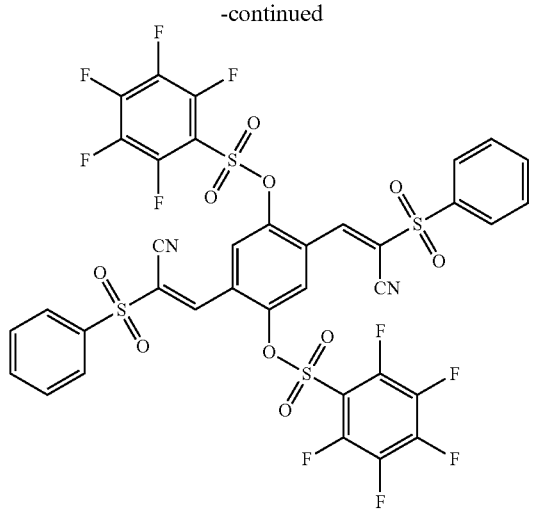
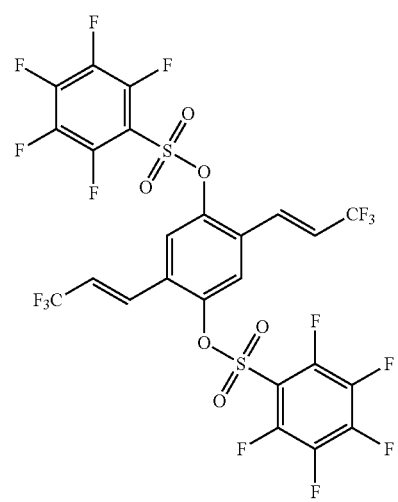
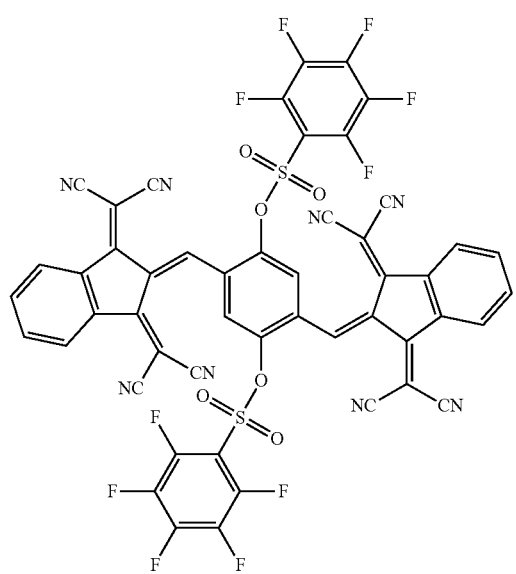
18
-continued
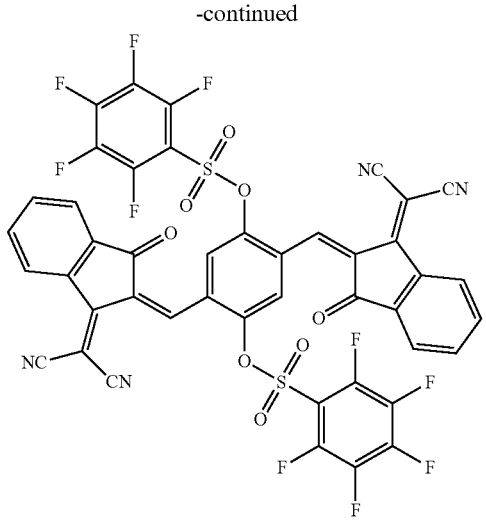
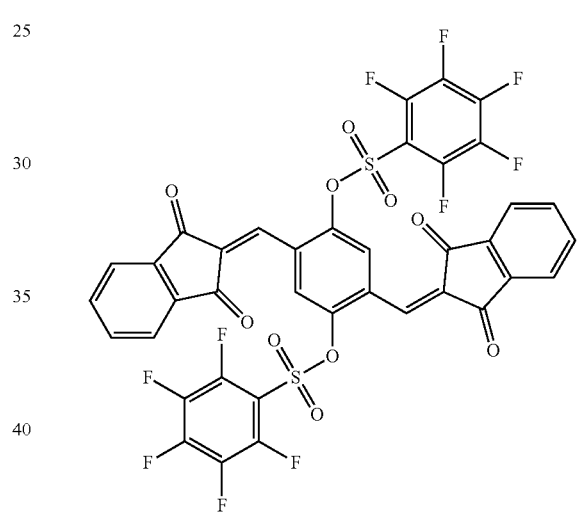
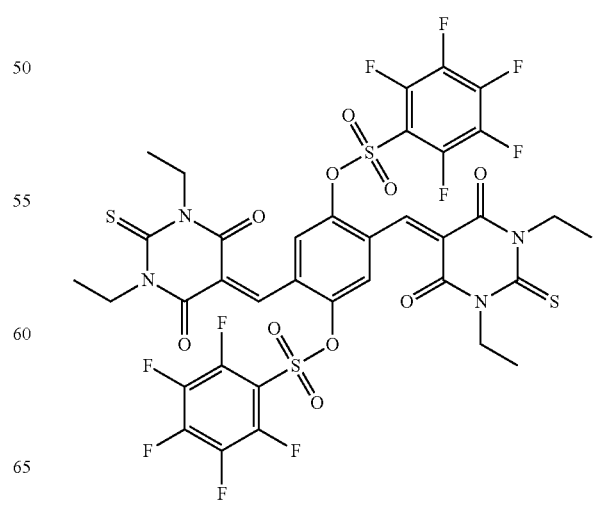

-continued

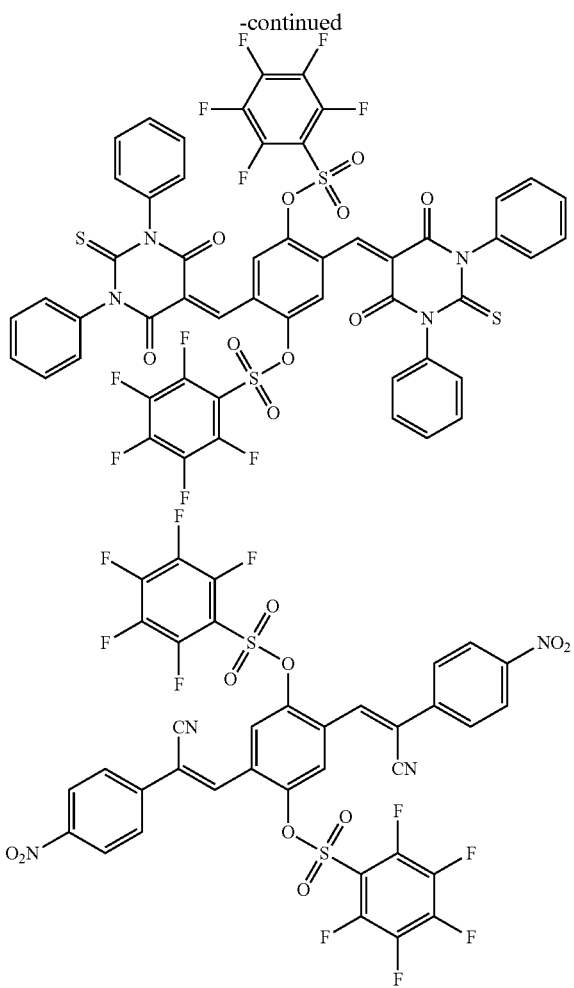

Meanwhile, upon existence of a target material, the fluorescent nanoprobe, from which fluorescence is expressed (emitted) to be used for detection, may include the sulfonated benzene compound and water.

The sulfonated benzene compound content may be 0.0001 to 3% by weight of the entire fluorescent nanoprobes, and the water content may be 44 to 99.9898% by weight of the entire fluorescent nanoprobes.

The fluorescent nanoprobe proposed in this specification may further include hydrophobic organic base. The hydrophobic organic base content may be 0.0001 to 3% by weight of the entire fluorescent nanoprobes. The hydrophobic organic base may be at least one selected from a group consisting of imidazole system, trialkylamine system and pyridine system.

The fluorescent nanoprobe may further include surfactant, and the surfactant content may be 0.01 to 50% by weight of the entire fluorescent nanoprobes. The surfactant may be at least one selected from a group consisting of poloxamer, polysorbate and sorbitan alkylester.

The fluorescent nanoprobe may also further include an organic base and surfactant at the same time. Here, the fluorescent nanoprobe may have a core-shell structure having a core consisting of the sulfonated benzene compound and the organic base and a shell consisting of the surfactant and water.

When the fluorescent nanoprobe further includes the organic base and the surfactant, the sulfonated benzene compound content may be 0.0001 to 3% by weight, the organic base content may be 0.0001 to 3% by weight, the surfactant content may be 0.01 to 50% by weight and the water content may be 44 to 99.9898% by weight.

The fluorescence nanoprobe may be nanoparticle of 10 to 200 nm in diameter.

For detection of hydrogen peroxide, a hydrogen peroxide detection solution, which the sulfonated benzene compound is dissolved in an organic solvent, may be used as it is. The hydrogen peroxide detection solution may be prepared by mixing the organic solvent with the sulfonated benzene compound of Chemical Formula 3, especially, with the sulfonated benzene compound of Chemical Formula 4.

A fluorescent nanoprobe fabrication method may include (a) mixing an organic solvent with the sulfonated benzene compound of Chemical Formula 3, and (b) removing the organic solvent to obtain fluorescent nanoprobes.

The step (b) may be carried out to obtain the fluorescent nanoprobes by first removing the organic solvent and adding water or first adding water and removing the organic solvent.

The sulfonated benzene compound in the fluorescent nanoprobe fabrication method may be the sulfonated benzene compound of Chemical Formula 4.

At the step (a), a surfactant may also be mixed, or an organic base may also be mixed.

After the step (b), the method may further include (c) obtaining aqueous-dispersed nanoprobes by dispersing the fluorescent nanoprobes in water.

Hereinafter, description will be given in more detail with reference to the accompanying drawings.

This specification relates to fluorescent molecules corresponding to Chemical Formula 1, Chemical Formula 2 and Chemical Formula 3.

The fluorescent molecules of Chemical Formula 1 and FIG. 1 may preferably exhibit emission wavelengths in the range of 400 to 900 nm, namely, wavelength region of visible rays and near infrared rays by introduction of a functional group A, which accepts electrons to acquire efficient fluorescence in a solid and molecular aggregate state.

Especially, the electron accepter A of the fluorescent molecules of Chemical Formula 1 may be at least one selected from a group consisting of ethylester (DT), aldehyde (AD), dimalonitrile (DM), nitrophenylacetonitrile (NN), phenylsulfonylacetonitrile (SN) and tetramalonitrileindan (TM), each having the electron-acceptors (A) coupled thereto, as shown in Chemical Formula 2.

Also, this specification relates to aqueous-dispersed fluorescent nanoprobe containing hydrophobic sulfonated benzene compound sensitive to hydrogen peroxide, hydrophobic organic base, surfactant and water.

The hydrophobic sulfonated benzene compound content may be 0.0001 to 3% by weight, the hydrophobic organic base content may be 0.0001 to 3% by weight, the surfactant content may be 0.01 to 50% by weight, and water content may be 44 to 99.9898% by weight, of the total weight of the fluorescent nanoprobe-dispersed aqueous dispersion solution.

The hydrophobic sulfonated benzene compound sensitive to the hydrogen peroxide may have a molecular structure represented by Chemical Formula 3, in which hydroxyl group of fluorescent molecules of Chemical Formula 1 is sulfonated using pentafluorobenzensulfonyl chloride. The hydrophobic sulfonated benzene compound sensitive to the hydrogen peroxide may be a molecule prepared by sulfonating at least one selected from a group consisting of diethyl 2,5-dihydroxyterephthalate (DT), 2,5-dihydroxyterephthalaldehyde (AD), 2,2'-(2,5-dihydroxy-1,4-phenylene)bis(methane-1-yl-1-ylidene)dimalonitrile (DM), (2Z,2Z')-3,3'-(2,5-dihydroxy-1, 4-phenylene)bis(2-(4-nitrophenyl)acrylonitrile (NN), (2Z,2Z')-3,3'-(2,5-dihydroxy-1,4-(phenylsulfonyl)acrylonitrile (SN), and 2,2',2",2'''-(2,2'-dihydroxy-1,4-phenylene)bis(methane-1-yl-1-ylidene)bis(1H-indene-3,2,1(2H)-trylidene)tetramalonitrile (TM), according to Chemical Formula 2.

An organic base may be used to catalyze a reaction between hydrogen peroxide and chemiluminescence probes in a hydrogen peroxide detection method by using chemiluminescence. In this specification, in order to accelerate a slow reaction between hydrogen peroxide and sulfonated benzene compound, a fast reaction was derived by employing a double catalytic function, which hydrophobic organic base and sulfonated benzene compound are integrated within a nanospace to lower activation energy of reaction and simultaneously shorten a distance between reactive molecules. Therefore, the hydrophobic organic base is an organic molecule, which is uniformly mixed with the hydrogen peroxide-sensitive sulfonated benzene compound and surfactant to create nanoparticles and catalyze the reaction with the hydrogen peroxide. The hydrophobic organic base may preferably be at least one selected from a group consisting of imidazole system (1-phenylimidazole, 2-phenylimidazole, 4-phenylimidazole, etc.), trialkylamine system (trihexylamine, etc.) and pyridine system.

The surfactant may function as a support for sustaining a structure of a core containing hydrophobic sulfonated benzene compound and hydrophobic organic base, as well as functioning as a surfactant. In order to utilize the nanoprobes for biological and medical purposes, the surfactant may preferably be a biocompatible surfactant for dispersion stability and biocompatibility in a physiological environment. For the purpose of chemical analysis, other surfactants may also be applicable.

Therefore, the surfactant may preferably be at least one selected from a group consisting of poloxamer, polysorbate and sorbitan alkylester.

Especially, the surfactant may be poloxamer consisting of pluronic®F-38, pluronic®F-68, pluronic®F-77, pluronic®F-87, pluronic®F-88, pluronic®F-98, pluronic®F-127 and pluronic®P-181 and pluronic®P-407 (BASF registered trademark), polysorbate consisting of tween®R-20, tween®R-40, tween®R-60 and tween®R-80 (Registered trademark of ICI Americas Inc.), and sorbitan alkylester consisting of span® 20, span® 40, span® 60, span® 65, span® 80 and span® 85 (Registered trademark of Croda International PLC).

The poloxamer, especially, pluronic®F-127 and F-68, may form micelle or hydrogel, thus to be widely used as a drug carrier for drugs in a pharmaceutical field or contrast agents for molecular imaging. A central portion of the nano structure of the poloxamer is relatively hydrophobic, so hydrophobic molecules may be easily contained in the central portion. Also, the surface of the poloxamer is surrounded by polyethylenglycol (PEG), which has hydrophilicity and anti-fouling property, so as to allow the nanoprobe to be applicable even for detection of hydrogen peroxide in vivo.

The aqueous-dispersed fluorescent nanoprobe may be 5 to 500 nm in diameter, preferably, 10 to 200 nm in diameter because the nanoprobe may be suitable to be used for clinic and diagnosis when the nanoparticles are present within the diameter range [Document 7: D. Peer et al., Nature Nanotech. 2: 751-760 (2007)].

A method for fabricating the aqueous-dispersed fluorescent nanoprobe may include (a) dissolving hydrogen peroxide-sensitive hydrophobic sulfonated benzene compound, hydrophobic organic base and surfactant in an organic solvent and removing the organic solvent to uniformly secure the mixture, and (b) adding water into the mixture of the step (a) to prepare a nanoprobe aqueous dispersion solution consisting of hydrogen peroxide-sensitive hydrophobic sulfonated benzene compound, hydrophobic organic base and surfactant.

The organic solvent at the step (a) may be at least one selected from a group consisting of dichloromethane, tetrahydrofuran, chloroform, ethylacetate and methanol. The organic solvent may be removed by evaporation at room temperature.

The water at the step (b) may be distilled water. The amount of water may be 2 to 10000 times with respect to the total weight of the fluorescent nanoprobes.

EXAMPLE

Hereinafter, description will be described in more detail according to Examples. However, those examples are merely illustrative, and should not be construed to limit this specification.

Example 1

Fluorescent Molecule Synthesis and Nanoparticle Fabrication and Fluorescence Characteristic Analysis (1) Synthesis of 2,5-dihydroxybenzene-1,4-dicarboaldehyde (AD)

0.5 g of 2,5-dimethoxybenzene-1,4-dicarboaldehyde (AD) and 25 mL of boron tribromide were dissolved in 150 mL of chlorobenzene and stirred at room temperature for 12 hours. After complete reaction, the reacted mixture was neutralized with sodium carbonate, followed by extraction with water and dichloromethane and recrystallization within dichloromethane, thereby obtaining 2,5-dihydroxybenzene-1,4-dicarboaldehyde. The obtained product exhibited yield, property and NMR analysis result as follows.

70% Yield, Yellow crystal, H-NMR (300 MHz, DMSO, TMS): δ=10.30 (s, 2H), 7.20 (s, 2H; aromatic)

(2) Synthesis of Fluorescent Molecules (DM, SN, NN, TM)

Several types of electron acceptors were introduced in 1,4-position of benzene ring containing 2,5-dihydroxyl group, thereby synthesizing molecules exhibiting fluorescence with various wavelengths. 2 equivalents of each of malonitrile, 2-(4-nitrophenyl)acetonitrile, 2-(phenylsulfonyl)acetonitrile, 1,3-bis(dicyanomethylidene)indan were dissolved in ethanol together with 1 equivalent of 2,5-dihydroxybenzene-1,4-dicarboaldehyde and stirred at 80° C. for 6 hours. Each precipitate generated after reaction was filtered and recrystallized in ethanol. The structures of the obtained products were analyzed using NMR. The structures of the fluorescent dyes, which were obtained as aforementioned, were shown in FIG. 1. The products exhibited yields, properties and NMR results as follows. FIG. 1 shows a representative drawing of fluorescence molecules prepared by Examples (1) and (2) and chemical structural formulas of DT, AD, DM, MN, SN and TM, to which electron acceptors A are coupled.

DM: 56% yield, yellow powder, $^1$H-NMR (300 MHz, DMSO, TMS): δ=8.94 (s, 2H), 7.92 (s, 2H; aromatic).

SN: 56% yield, yellow powder, $^1$H-NMR (300 MHz, DMSO, TMS): δ=9.19 (s, 2H), 8.17 (s, 2H; aromatic), 8.02 (d, 4H; aromatic), 7.77 (t, 2H; aromatic), 7.70 (t, 4H; aromatic).

NN: 64% yield, yellow powder, $^1$H-NMR (300 MHz, DMSO, TMS): δ=8.36 (d, 4H; aromatic), 8.26 (s, 2H), 8.01 (d, 4H; aromatic), 7.16 (s, 2H; aromatic).

TM: 47% yield, red powder, $^1$H-NMR (300 MHz, DMSO, TMS): δ=10.28 (s, 2H), 7.91 (d, 4H; aromatic), 7.39 (d, 4H; aromatic), 7.22 (s, 2H; aromatic), 5.71 (s, 2H; hydroxy).

(3) Nanoparticle Fabrication and Fluorescence Characteristic Analysis

The fluorescent molecules synthesized in Example 1-(2), diethyl 2,5-dihydroxyterephthalate (DT) and 1-phenylimidazole, which is a hydrophobic organic base, were integrated into a core of pluronic®F-68 micelles so as to prepare nanoparticles whose fluorescence characteristics were then evaluated.

To prepare the nanoparticles, first, 10 mg of pluronic®F-68, 0.01 mg of each of fluorescent molecules and DT synthesized in Example 1-(2) and 1 mg of 1-phenylimidazole were dissolved in 0.3 mL of dichloromethane and uniformly mixed. Afterwards, solvent was evaporated at room temperature.

1 mL of distilled water was then added into the dried mixture and mixed uniformly, thereby preparing aqueous-dispersed nanoparticles each having a core in which fluorescent molecules and hydrophobic organic base were accumulated.

Figure 2:
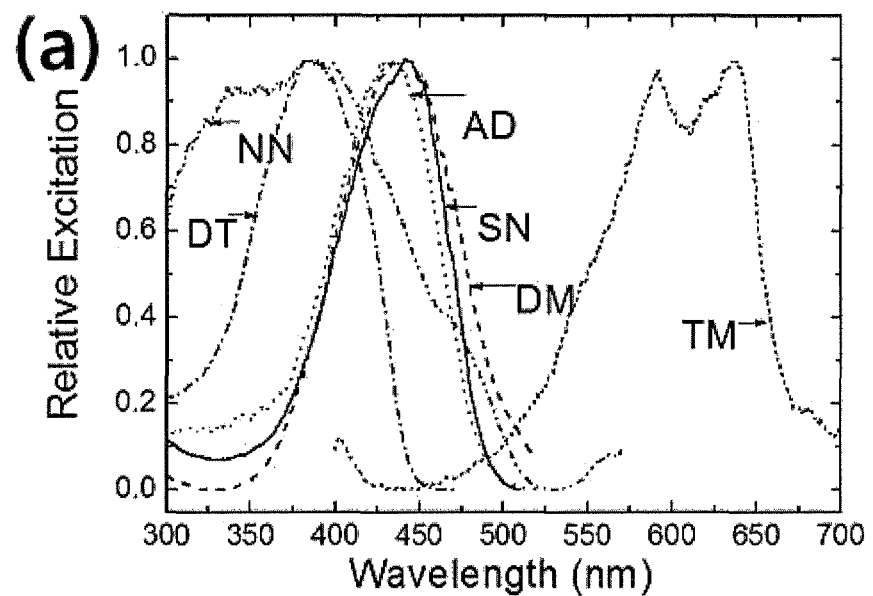
FIGS. 2A and 2B respectively show excitation and fluorescence spectra of aqueous-dispersed fluorescent nanoparticles fabricated by the method of Example 1-(3)
Figure 2:
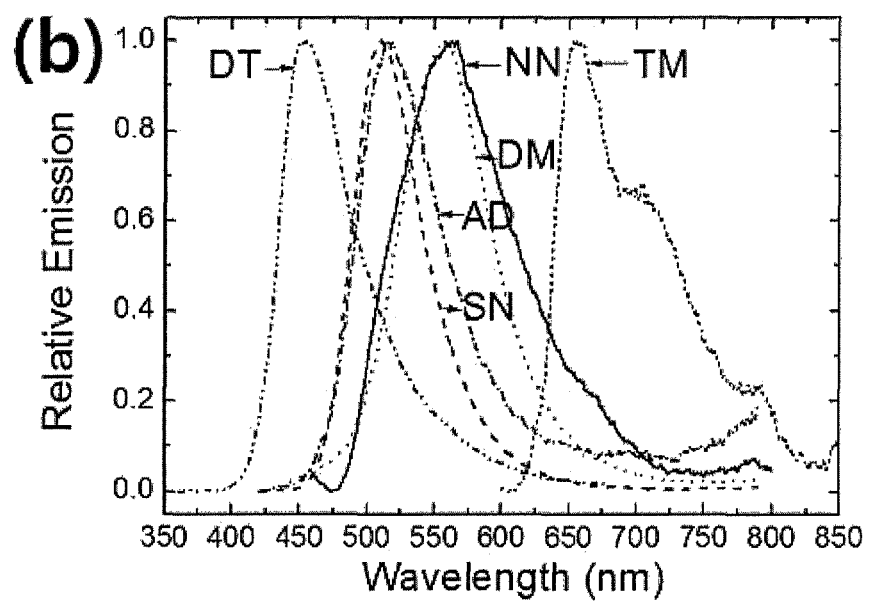

To analyze fluorescence characteristics of the prepared nanoparticles, a fluorescent spectrum for each aqueous dispersion and an excitation spectrum for the fluorescence were obtained by using a fluorescence spectrophometer (Hitachi F-7000) and are shown in FIGS. 2B and 2A, respectively. FIG. 2 shows an excitation spectrum (A) and fluorescence spectrum (B) of the aqueous-dispersed fluorescent nanoparticles prepared by the method of Example 1-(3).

As can be seen in the fluorescence spectrum, the fluorescence is emitted within a wide range of 400 to 800 nm depending on an electron-withdrawing strength of a substituted electron acceptor, whereby a fluorescence wavelength can be selected according to use in wide fields such as biology, medical science, chemical analysis and the like.

Also, as can be seen in the excitation spectrum, excitation light is also selectable within a wide range of 300 to 670 nm.

Example 2

Synthesis of Hydrogen Peroxide-Sensitive Sulfonated Benzene Compound and Fabrication of Fluorescent Nanoprobe with the Same (1) Synthesis of diethyl 2,5-bis(pentafluorophenyl)sulfonyl)oxy)terephthalate (FSDT)

The structure and use of pentafluorophenyl sulfonate, as a functional group, which was separated by reaction with hydrogen peroxide to derive fluorescence changes, were understood with reference to the previous patent applications [Document 8: Hatsuo Meada et al., and USA Patent Application No. U.S. Pat. No. 7,491,832 B2].

0.2 g of DT was dissolved in 5 mL of tetrahydrofuran. The DT solution was then mixed with 0.5 g of pentafluorobenzenesulfonyl chloride and 0.2 mL of triethylamine, followed by reaction at room temperature for 6 hours. Afterwards, a crystalline material was removed by filtration. The obtained mixture was re-precipitated in ethyl acetate to obtain a product. The product exhibited the following yield, property and NMR analysis result.

92% Yield, white powder, $^1$H-NMR (300 MHz, CDCl$_3$, TMS): δ=7.88 (s, 2H; aromatic), 4.38 (q, 4H), 1.42 (t, 6H).

(2) Fabrication of Aqueous-Dispersed Fluorescent Nanoprobe 10 mg of pluronic®F-68, 0.1 mg of FSDT as the hydrogen peroxide-sensitive hydrophobic sulfonated benzene compound, which was synthesized in Example 2-(1), and 1 mg of an organic base selected from 1-phenylimidazole, 2-phenylimidazole, 4-phenylimidazole and trihexylamine were dissolved in 0.3 mL of dichloromethane and uniformly mixed. Solvent was then evaporated at room temperature.

Afterwards, 1 mL of distilled water was added into the dried mixture and uniformly mixed, thereby preparing aqueous-dispersed nanoparticles, each having a core in which fluorescent probes and basic molecules were accumulated.

Figure 3:
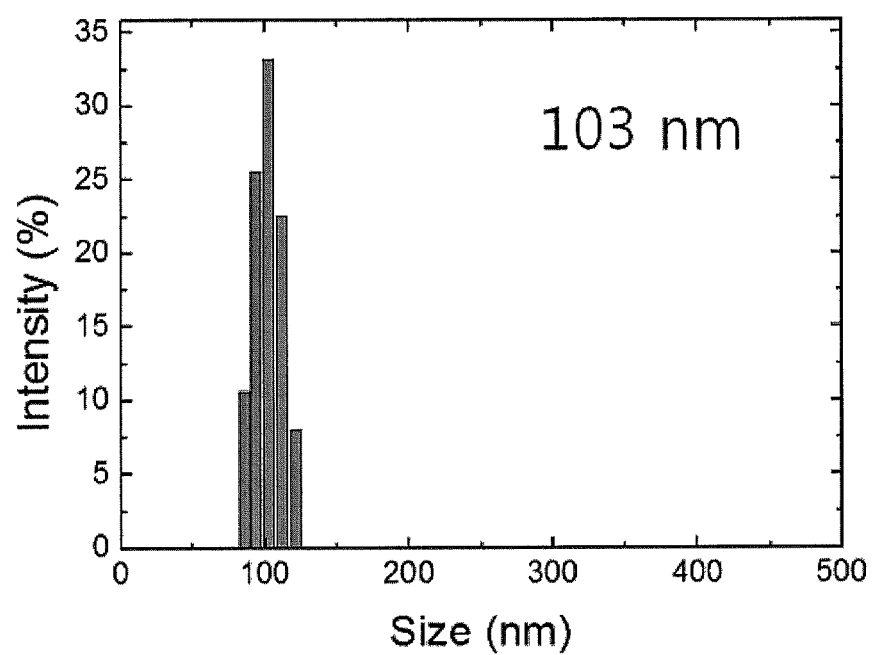
FIG. 3 is a graph showing distribution of particle sizes measured by dynamic light scattering of the aqueous-dispersed fluorescent nanoprobe fabricated by the method of Example 2-(2)

The distribution of particle sizes of the prepared aqueous-dispersed nanoprobes was measured by BI-9000AT digital autocorrelator, (Brookhaven), and the measured results were shown in FIG. 3. FIG. 3 is a graph showing particle size distribution of the aqueous-dispersed nanoprobes prepared by the method of Example 2-(2), measured by the BI-9000AT digital autocorrelator.

As shown in FIG. 3, the fluorescent nanoprobes exhibited the particle size distribution that an average diameter was 103 nm in an aqueous-dispersed state.

Example 3

Figure 4:
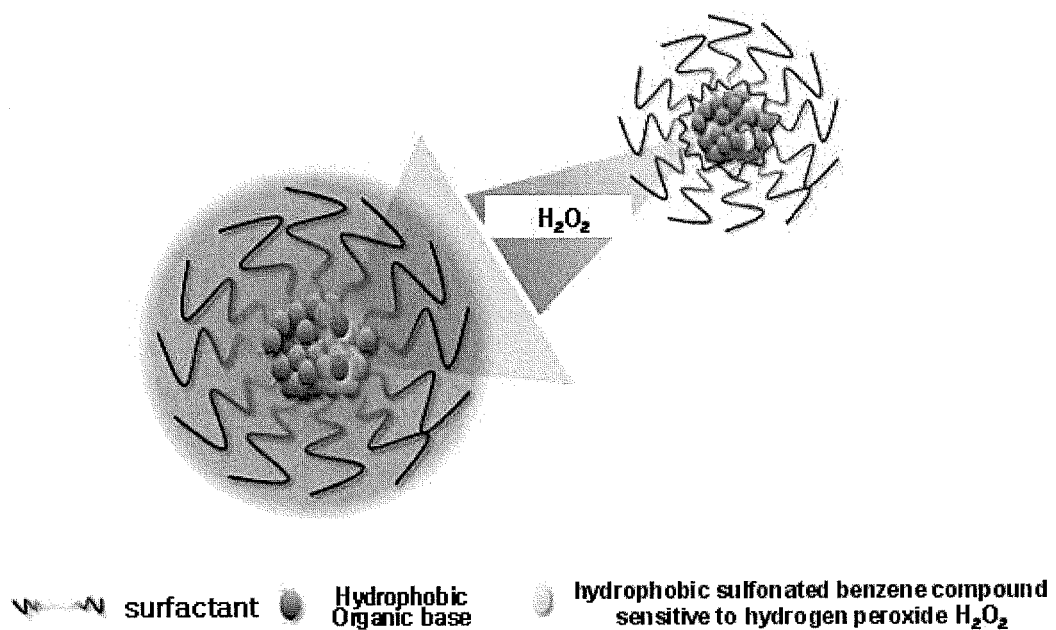
FIG. 4 is a schematic representation of fluorescence generation by reaction between aqueous-dispersed fluorescent nanoprobes and hydrogen peroxide.

Hydrogen Peroxide Detection Characteristic Evaluation of Aqueous-Dispersed Fluorescent Nanoprobe (1) Reaction Acceleration Function Test of Hydrophobic Organic Base FIG. 4 is a schematic diagram of fluorescence generation in response to reaction between aqueous-dispersed fluorescent nanoprobes and hydrogen peroxide. In regard of the aqueous-dispersed fluorescent nanoprobes described in this specification, as shown in FIG. 4, the reaction between the hydrogen peroxide-sensitive sulfonated benzene compound and hydrogen peroxide may be accelerated by the hydrophobic organic base integrated in the nanoparticles, thereby allowing an extremely fast detection of the hydrogen peroxide.

Figure 5:
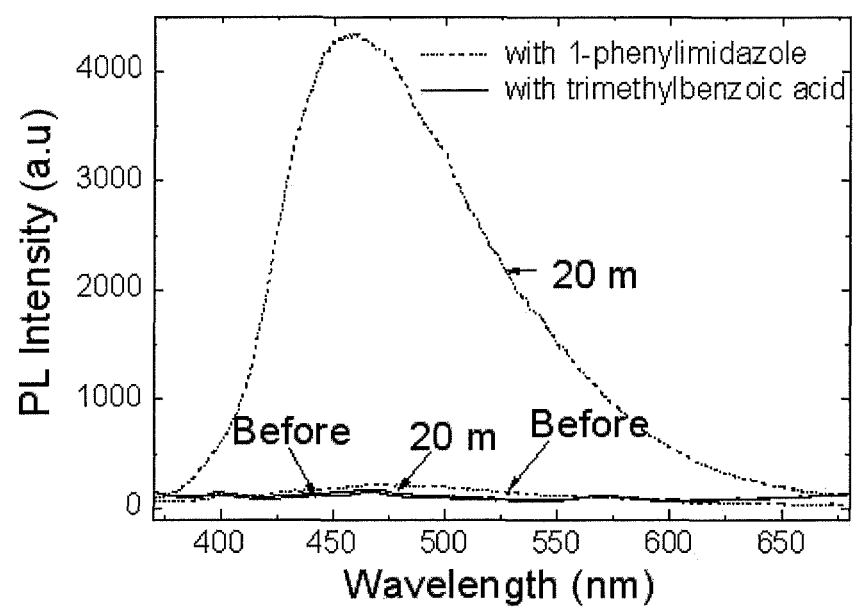
FIG. 5 shows fluorescence spectra, measured by a function evaluation of hydrophobic organic base of Example 3-(1), before addition of hydrogen peroxide and 20 minutes after addition of the hydrogen peroxide (dotted line: aqueous-dispersed fluorescent nanoprobe with 1-phenylimidazole, solid line: aqueous-dispersed fluorescent nanoprobe with trimethylbenzoic acid)

To prove the reaction acceleration effect of the organic base, nanoprobes each having a central portion, in which the hydrogen peroxide-sensitive sulfonated benzene compound and 1,3,5-trimethylbenzoic acid as acid molecules were integrated, were prepared as a control group by the same method as Example 2-(2). 0.4 mmol of hydrogen peroxide was added into 1 mL of the prepared control group of aqueous-dispersed nanoprobes and 1 mL of the aqueous-dispersed fluorescent nanoprobes with 1-phenylimidazole prepared by Example 2-(2), respectively. After 20 minutes, fluorescence spectra thereof were observed, and the results were shown in FIG. 5. FIG. 5 shows fluorescence spectra, measured by a function evaluation of hydrophobic organic base of Example 3-(1), before addition of hydrogen peroxide and 20 minutes after addition of the hydrogen peroxide (dotted line: aqueous-dispersed fluorescent nanoprobe with 1-phenylimidazole, solid line: aqueous-dispersed fluorescent nanoprobe with trimethylbenzoic acid).

The fluorescence of the control group with 1,3,5-trimethylbenzoic acid was increased by 1.2 times even after 20 minutes elapsed, which exhibited a rare fluorescence change. On the other hand, the fluorescence of the aqueous-dispersed fluorescent nanoprobe with the 1-phenylimidazole was increased by 23 times, from which it was understood that the reaction rate was increased by the organic base.

(2) Acceleration Function Evaluation of Hydrogen Peroxide Detection According to Organic Base It was observed that the organic base of Example 3-(1) accelerated the hydrogen peroxide detection reaction. Thus, the difference of acceleration function depending on types of bases was evaluated in this Example.

Figure 6:
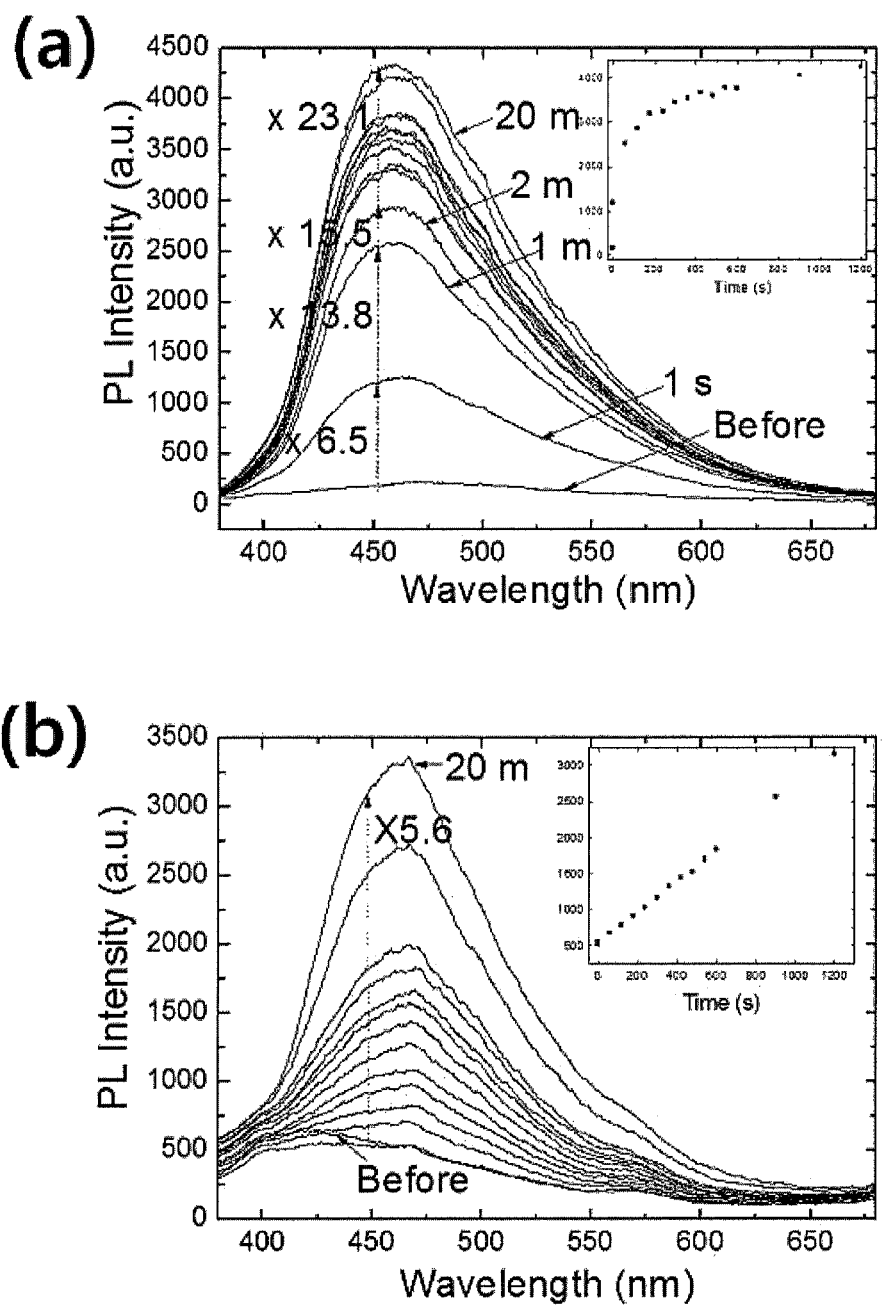
FIG. 6 is a graph (graph inserted in an upper right side) showing different kinetics of temporal evolution of fluorescence signal in response to the detection of hydrogen peroxide according to a type of hydrophobic organic base of Example 3-(2) (dotted line: aqueous-dispersed fluorescent nanoprobe with 1-phenylimidazole, solid line: aqueous-dispersed fluorescent nanoprobe with 2-phenylimidazole).

1 mL of the aqueous-dispersed fluorescent nanoprobes with 1-phenylimidazole, 2-phenylimidazole, 4-phenylimidazole and trihexylamine, prepared by Example 2-(2), was mixed with 0.4 mmol of hydrogen peroxide, and thereafter fluorescence spectra were observed on a time basis. Among the thusly-obtained results, the results from the nanoprobes with the 1-phenylimidazole and the 2-phenylimidazole were shown in FIG. 6. FIG. 6 is a graph (graph inserted in an upper right side) showing different kinetics of temporal evolution of fluorescence signal in response to the detection of hydrogen peroxide according to a type of hydrophobic organic base of Example 3-(2) (FIG. 6A shows the aqueous-dispersed fluorescent nanoprobe with 1-phenylimidazole, and FIG. 6B shows the aqueous-dispersed fluorescent nanoprobe with 2-phenylimidazole).

As soon as adding the hydrogen peroxide, the nanoprobe with 1-phenylimidazole exhibited an increase in the fluorescence strength by 6.5 times. Also, within 1 minute, the fluorescence intensity thereof was increased by about 14 times. Consequently, it was understood that the nanoprobes with 1-phenylimidazole exhibited a reaction rate enough to carry out a real-time detection of the hydrogen peroxide.

After addition of the hydrogen peroxide, the nanoprobe with 2-phenylimidazole exhibited a slow increase in fluorescence in proportion to time, and the nanoprobes with the 4-phenylimidazole and trihexylamine already exhibited considerably increased fluorescence before addition of the hydrogen peroxide. Hence, it was observed that the hydrogen peroxide detection characteristic differed depending on selection of an organic base.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A sulfonated benzene compound, from which fluorescence is quenched by sulfonation, the sulfonated benzene compound represented by the following Chemical Formula 3:

[Chemical Formula 3]

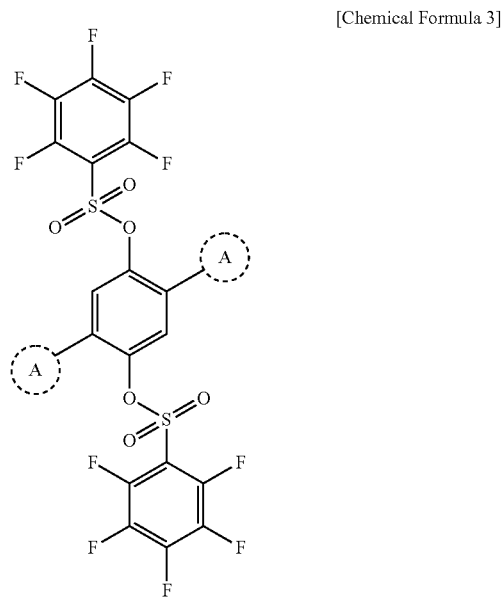

where A denotes at least one electron-accepting substituent selected from a group consisting of ester, aldehyde, nitrile, nitrobenzene, sulfonated benzene, indan, barbituric acid and their derivatives.

2. The compound of claim 1, wherein the sulfonated benzene compound is represented by the following Chemical Formula 4:

[Chemical Formula 4]

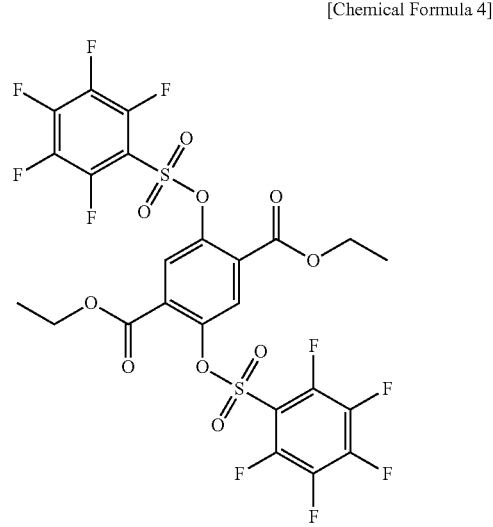

27
-continued
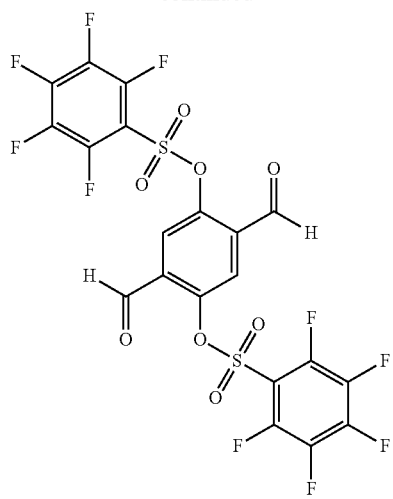
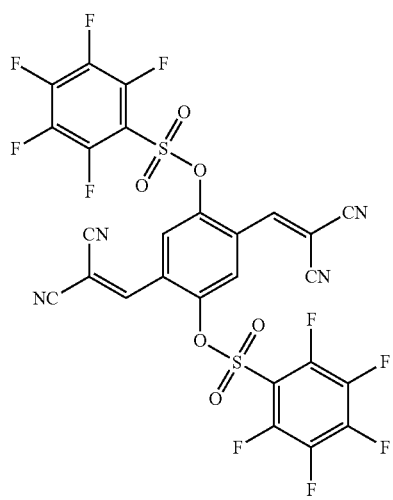
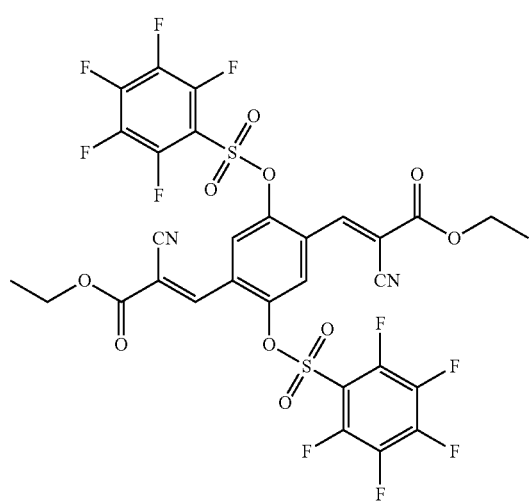
28
-continued
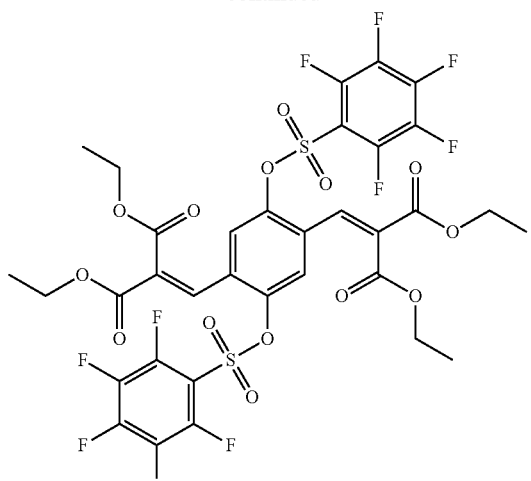
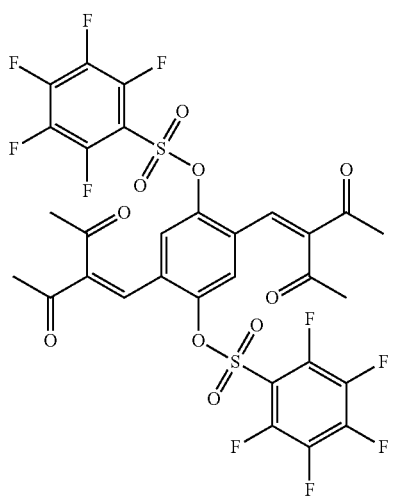
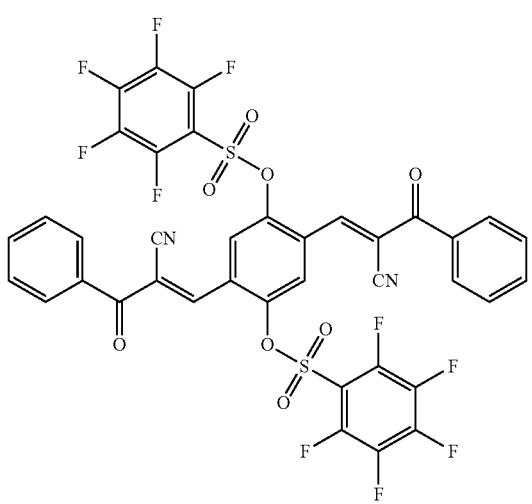

29
-continued
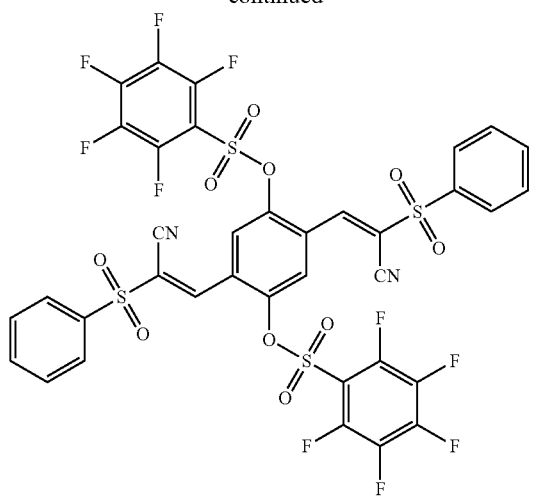
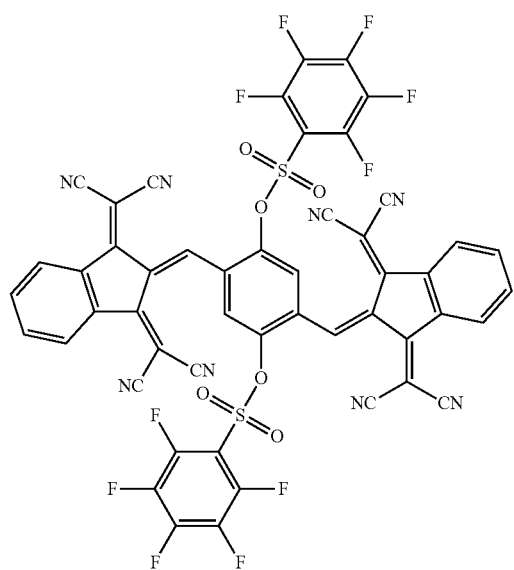
30
-continued
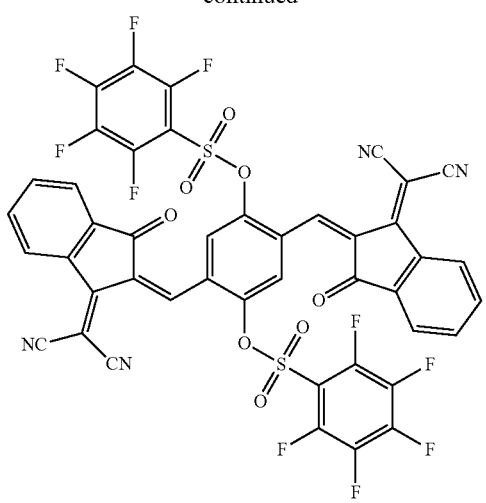
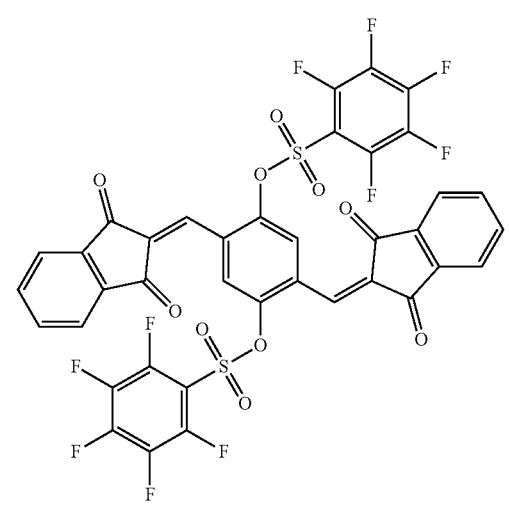
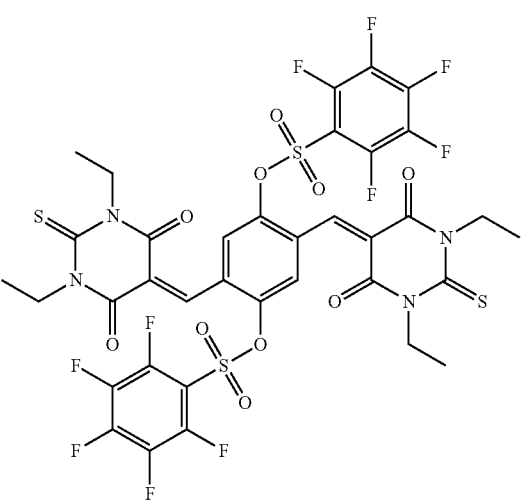

-continued

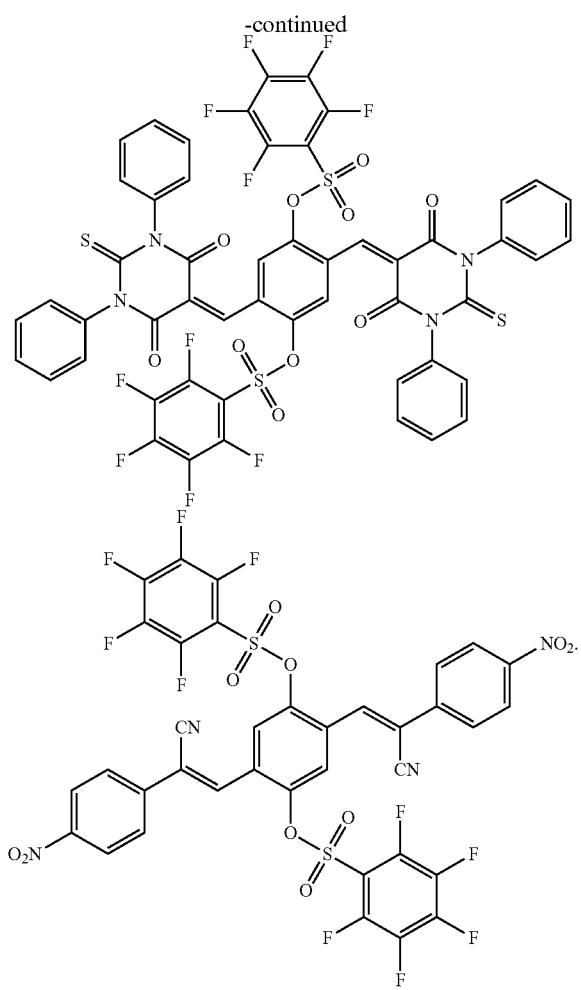

3. A fluorescent nanoprobe with the sulfonated benzene compound according to claim 1 and water.

4. The nanoprobe of claim 3, further comprising hydrophobic organic base.

5. The nanoprobe of claim 4, wherein the hydrophobic organic base is at least one selected from a group consisting of imidazole system, trialkylamine system and pyridine system.

6. The nanoprobe of claim 3, further comprising a surfactant.

7. The nanoprobe of claim 6, wherein the surfactant is at least one selected from a group consisting of poloxamer, polysorbate and sorbitan alkylester.

8. The nanoprobe of claim 3, further comprising an organic base and surfactant, wherein the fluorescent nanoprobe has a core-shell structure having a core consisting of the sulfonated benzene compound and the organic base and a shell consisting of the surfactant and water.

9. The nanoprobe of claim 8, wherein the sulfonated benzene compound content is 0.0001 to 3% by weight, the organic base content is 0.0001 to 3% by weight, the surfactant content is 0.01 to 50% by weight and the water content is 44 to 99.9898% by weight.

10. A hydrogen peroxide detection solution, which the sulfonated benzene compound of claim 1 is dissolved in an organic solvent.

* * * * *